US005962653A

United States Patent [19]

Boyd et al.

[11] Patent Number: 5,962,653

[45] Date of Patent: Oct. 5, 1999

[54] **METHODS OF OBTAINING ANTIVIRAL PROTEINS AND ANTIVIRAL PEPTIDES FROM *NOSTOC ELLIPSOSPORUM***

[75] Inventors: Michael R. Boyd, Ijamsville; Kirk R. Gustafson, Frederick, both of Md.

[73] Assignee: The United States of America as represented by the Department of Health and Human Services, Washington, D.C.

[21] Appl. No.: 08/969,584

[22] Filed: Nov. 13, 1997

Related U.S. Application Data

[62] Division of application No. 08/429,965, Apr. 27, 1995.

[51] Int. Cl.[6] .............................. C07K 1/14; C07K 1/20

[52] U.S. Cl. .............................. 530/417; 530/412

[58] Field of Search .............................. 530/412, 417

[56] References Cited

FOREIGN PATENT DOCUMENTS

WO 93/06216 4/1993 WIPO .

OTHER PUBLICATIONS

Abuchowski et al., "Soluble Polymer–Enzyme Adducts," in *Enzymes as Drugs*, Holcenberg et al., eds., John Wiley: New York, 1981, pp. 367–383.

Abuchowski et al., Alteration of Immunological Properties of Bovine Serum Albumin by Covalent Attachment of Polyethylene Glycol, *Journal of Biological Chemistry*, 252(11), 3578–3581 (1977).

Aullo et al., "A Recombinant Diphtheria Toxin Related Human CD4 Fusion Protein Specifically Kills HIV Infected Cells Which Express gp120 But Selects Fusion Toxin Resistant Cells Which Carry HIV," *EMBO Journal*, 11(2), 575–583 (1992).

Balter, "UN Readies New Global AIDS Plan," *Science*, 266, 1312–1313 (1994).

Banga et al., "Systemic Delivery of Therapeutic Peptides and Proteins," *International Journal of Pharmaceutics*, 48, 15–50 (1988).

Barry, "The Transdermal Route for the Delivery of Peptides and Proteins," in *Delivery Systems for Peptide Drugs*, Davis et al., eds., Plenum Press: New York, 1986, pp. 265–275.

Berzofsky, "Approaches and Issues in the Development of Vaccines Against HIV," *Journal of Acquired Immune Deficiency Syndromes*, 4, 451–459 (1991).

Bird, "The Use of Spermicide Containing Nonoxynol–9 in the Prevention of HIV Infection," *AIDS*, 5(7), 791–796 (1991).

Bourinbaiar et al., "Anti–HIV Effect of Gramicidin In Vitro: Potential for Spermicide Use," *Life Sciences*, 54(1), 5–9 (1994).

Bourinbaiar et al., "Comparative In Vitro Study of Contraceptive Agents with Anti–HIV Activity: Gramicidin, Nonoxynol–9, and Gossypol," *Contraception*, 49, 131–137 (1994).

Boyd, "Strategies for the Identification of New Agents for the Treatment of AIDS: A National Program to Facilitate the Discovery and Preclinical Development of New Drug Candidates for Clinical Evaluation," *AIDS Etiology, Diagnosis, Treatment, and Prevention*, Second Edition, DeVita et al., eds., J.B. Lippincott Company, 1988, pp. 305–317.

Boyd et al., "Anit–HIV Michellamines from *Ancistrocladus korupensis*," *Journal of Medicinal Chemistry*, 37(12), 1740–1745 (1994).

Capon et al., "Designing CD4 Immunoadhesins for AIDS Therapy," *Nature*, 337, 525–531 (1989).

Capon et al., "The CD4–gp120 Interaction and AIDS Pathogenesis," *Annu. Rev. Immunol.*, 9, 649–678 (1991).

Carone et al., "Renal Tubular Processing of Small Peptide Hormones," *The Journal of Laboratory and Clinical Medicine*, 100(1), 1–14 (1982).

Carter et al., "Structure of Majusculamide C, a Cyclic Depsipeptide from *Lyngbya majuscula*," *J. Org. Chem.*, 49, 236–241 (1984).

Chaudhary et al., "Selective Killing of HIV–Infected Cells by Recombinant Human CD4–Pseudomonas Exotoxin Hybrid Protein," *Nature*, 335, 369–372 (1988).

Chaudhary et al., "CD4–PE40—A Chimeric Toxin Active Against Human Immunodeficiency Virus (HIV)–Infected Cells," *The Human Retroviruses*, pp. 379–387.

Coffin, John M., "HIV Population Dynamics In Vivo: Implications for Genetic Variation, Pathogenesis, and Therapy," *Science*, 267, 483–489 (1995).

Cohen, "High Turnover of HIV in Blood Revealed by New Studies," *Science*, 267, 179 (1995).

Coll et al., "The Application of Vacuum Liquid Chromatograph to the Separation of Terpene Mixtures," *Journal of Natural Products*, 49(5), 934–936 (1986).

Davey et al., "Use of Recombinant Soluble CD4 Pseudomonas Exotoxin, a Novel Immunotoxin, for Treatment of Persons Infected with Human Immunodeficiency Virus," *Journal of Infectious Diseases*, 170, 1180–1188 (1994).

Davis, "Delivery Systems for Bipharmaceuticals," *J. Pharm. Pharmacol.*, 44(Suppl. 1), 186–190 (1992).

De Clercq, "Antiviral Agents: Characteristic Activity Spectrum Depending on the Molecular Target with Which They Interact," *Advances In Virus Research*, 42, 1–55 (1993).

De Clercq, "Basic Approaches to Anti–Retroviral Treatment," *Journal of Acquired Immune Deficiency Syndromes*, 4(3), 207–218 (1991).

Deasy et al., in *Microencapsulation and Related Processes*, Swarbrick J., ed., Marcel Dekker, Inc.: New York, 1984, pp. 1–60.

(List continued on next page.)

*Primary Examiner*—Elizabeth Kemmerer
*Attorney, Agent, or Firm*—Leydig, Voit & Mayer, Ltd.

[57] ABSTRACT

The present invention provides antiviral proteins, peptides and conjugates, as well as methods of obtaining these agents. The antiviral proteins, peptides and conjugates of the present invention can be used alone or in combination with other antiviral agents in compositions, such as pharmaceutical compositions, to inhibit the infectivity, replication and cytopathic effects of a virus, such as a retrovirus, in particular a human immunodeficiency virus, specifically HIV-1 or HIV-2, in the treatment or prevention of viral infection.

3 Claims, 12 Drawing Sheets

OTHER PUBLICATIONS

Emtage, "Biotechnology and Protein Production," in *Delivery Systems for Peptide Drugs*, Davis et al., eds., Plenum Press: New York, 1986, pp. 23–33.

Eppstein et al., "Alternative Delivery Systems for Peptides and Proteins as Drugs," *CRC Critical Reviews in Therapeutic Drug Carrier Systems*, 5(2), 99–139 (1988).

Faulkner, "Marine Natural Products," *Natural Product Reports*, pp. 355–394 (1994).

Frankmölle et al., "Antifungal Cyclic Peptides from the Terrestrial Blue–Green Alga *Anabaena laxa*," *The Journal of Antibiotics*, 45(9), 1451–1457 (1992).

Freed et al., "The Role of the HIV Envelope Glycoproteins in Cell Fusion and the Pathogenesis of AIDS," *Bull. Inst. Pasteur*, 88, 73–110 (1990).

Glombitza et al., in *Algal and Cyanobacterial Biotechnology*, Cresswell, R.C., et al., eds., 1989, pp. 211–218.

Gulakowski et al., "A Semiautomated Multiparameter Approach for Anti–HIV Drug Screening," *Journal of Virological Methods*, 33, 87–100 (1991).

Gustafson et al., "A Nonpromoting Phorbol from the Samoan Medicinal Plant *Homalanthus nutans* Inhibits Cell Killing by HIV–1," *J. Med. Chem*, 35, 1978–1986 (1982).

Guyden, "Techniques for Gene Cloning and Expression," in *Recombinant DNA Technology Concepts and Biomedical Applications*, Steinberg et al., eds., Prentice Hall: Englewood Cliffs, NJ, 1993, pp. 81–124 and 150–162.

Husson et al., "Phase 1 Study of Continuous–Infusion Soluble CD4 as a Single Agent and In Combination with Oral Dideoxyinosine Therapy in Children with Symptomatic Human Immunodeficiency Virus Infection," *The Journal of Pediatrics*, 121(4), 627–633 (1992).

Kashman et al., "The Calanolides, a Novel HIV–Inhibitory Class of Coumarin Derivatives from the Tropical Rainforest Tree, *Calophyllum lanigerum*," *Journal of Medicinal Chemistry*, 35(15), 2735–2743 (1992).

Koenig et al., "Selective Infection of Human CD4+ Cells by Simian Immunodeficiency Virus: Productive Infection Associated with Envelope Glycoprotein–Induced Fusion," *Proc. Natl. Acad. Sci. USA*, 86, 2443–2447 (1989).

Krishnamurthy et al., "Structural Characterization of Toxic Cyclic Peptides from Blue–Green Algae by Tandem Mass Spectrometry," *Proc. Natl. Acad. Sci. USA*, 86, 770–774 (1989).

Laemmli, "Cleavage of Structural Proteins During the Assembly of the Head of Bacteriophage T4," *Nature*, 227, 680–685 (1970).

Langner, "Antiviral Effects of Different CD4–Immunoglobulin Constructs Against HIV–1 and SIV: Immunological Characterization, Pharmacokinetic Data and In Vivo Experiments," *Arch. Virol.*, 130, 157–170 (1993).

Lin et al., "Selective Inhibition of Human Immunodeficiency Virus Type 1 Replication by the (–) but Not the (+) Enantiomer of Gossypol," *Animicrob. Agents Chemother.*, 33(12), 2149–2151 (1989).

Lipton, "HIV Displays Its Coat of Arms, " *Nature*, 367, 113–114 (1994).

Lisi et al., "Enzyme Therapy: I. Polyethylene Glycol:β–Glucuronidase Conjugates as Potential Therapeutic Agents in Acid Mucopolysaccharidosis," *J. Appl. Biochem.*, 4, 19–33 (1982).

Matsushita et al., "Characterization of a Human Immunodeficiency Virus Neutralizing Monoclonal Antibody and Mapping of the Neutralizing Epitope," *Journal of Virology*, 62(6), 2107–2114 (1988).

Maulding, "Prolonged Delivery of Peptides by Microcapsules," *Journal of Controlled Release*, 6, 167–176 (1987).

McCaffrey et al., "A Rapid Fluorometic DNA Assay for the Measurement of Cell Density and Proliferation In Vitro," *In Vitro Cellular & Developmental Biology*, 24(3), 247–252 (1988).

Merigan, "Treatment of AIDS with Combinations of Antiretroviral Agents," *The American Journal of Medicine*, 90(Supp. 4A), 8S–17S (1991).

Merson, "Slowing the Spread of HIV: Agenda for the 1990s," *Science*, 260, 1266–1268 (1993).

Michalowski et al., "A Novel Allophycocyanin Gene (apcD) from *Cyanophora paradoxa* Cyanelles," *Nucleic Acids Research*, 18(8), 2186 (1990).

Mitsuya et al., "Molecular Targets for AIDS Therapy," *Science*, 249, 1533–1544 (1990).

Moore et al., "Sensitive ELISA for the gp120 and gp160 Surface Glycoproteins of HIV–1," *AIDS Research and Human Retroviruses*, 4(5), 369–379 (1988).

Moore et al., "Virions of Primary Human Immunodeficiency Virus Type 1 Isolates Resistant to Soluble CD4 (sCD4) Neutralization Differ in sCD4 Binding and Glycoprotein gp120 Retention from sCD4–Sensitive Isolates," *Journal of Virology*, 66(1), 235–243 (1992).

Morgan et al., "Further Evaluation of Soluble CD4 as an Anti–HIV Type 1 Gene Therapy: Demonstration of Protection of Primary Human Peripheral Blood Lymphocytes from Infection by HIV Type 1," *AIDS Research and Human Retroviruses*, 10(11), 1507–1515 (1994).

Nicholl, in *An Introduction to Genetic Engineering*, Cambridge University Press: Cambridge, 1994, pp. 1–6 and 127–130.

Okino et al., "Microginin, An Angiotensin–Converting Enzyme Inhibitor from the Blue–Green Alga *Microcystis aeruginosa,*" *Tetrahedron Letters*, 34(3), 501–504 (1993).

Old et al., in *Principles of Gene Manipulation*, Blackwell Scientific Publishers: London, 1992, pp. 1–13 and 108–221.

Orloff et al., "Increase in Sensitivity to Soluble CD4 by Primary HIV Type 1 Isolates After Passage through C8166 Cells: Association with Sequence Differences in the First Constant (C1) Region of Glycoprotein 120," *AIDS Research and Human Retroviruses*, 11(3), 335–342 (1995).

Patterson et al., "Antiviral Activity of Cultured Blue–Green Algae (Cyanophyta)," *J. Phycol.*, 29, 125–130 (1993).

Patterson et al., "Antineoplastic Activity of Cultured Blue––Green Algae (Cyanophyta)," *J. Phycol.*, 27, 530–536 (1991).

Patton et al., "(D) Routes of Delivery: Case Studies (2) Pulmonary delivery of Peptides and Proteins for Systemic Action," *Advanced Drug Delivery Reviews*, 8, 179–196 (1992).

Pelletier et al., "Separation of Diterpenoid Alkaloid Mixtures Using Vacuum Liquid Chromatography," *Journal of Natural Products*, 49(5), 892–900 (1986).

Polsky et al., "Inactivation of Human Immunodeficiency Virus In Vitro by Gossypol," *Contraception*, 39(6), 579–587 (1989).

Ramachandran et al., "Failure of Short–Term CD4–PE40 Infusions to Reduce Virus Load in Human Immunodeficiency Virus–Infected Person," *Journal of Infectious Diseases*, 170, 1009–1013 (1994).

Rink et al., "Cytoplasmic pH and Free $Mg^{2+}$ in Lymphocytes," *Journal of Cell Biology*, 95, 189–196 (1982).

Rogers, "Ferredoxins, Flavodoxins and Related Proteins: Structure, Function and Evolution," *The Cyanobacteria*, P. Fay et al., eds., Elsevier Science Publishers B.V. (Biomedical Division), 1987, pp. 35–67.

Royer et al., "Inhibition of Human Immunodeficiency Virus Type 1 Replication by Derivatives of Gossypol," *Pharmacol. Res.*, 24(4), 407–412 (1991).

Rosenberg et al., "Commentary: Methods Women Can Use That May Prevent Sexually Transmitted Disease, Including HIV," *American Journal of Public Health*, 82(11), 1473–1478 (1992).

Rosenberg et al., "Virucides in Prevention of HIV Infection," *Sexually Transmitted Diseases*, 20(1), 41–44 (1993).

Rümbeli et al., "γ–N–Methylasparagine in Phycobiliproteins from the Cyanobacteria *Mastigocladus laminosus* and Calothrix," *FEBS Letters*, 221(1), 1–2 (1987).

Samenen et al., "Polypeptides As Drugs," in *Polymeric Materials in Medication*, Gebelein et al., eds., Plenum Press: New York, 1985, pp. 227–247.

Sanders, "Drug Delivery Systems and Routes of Administration of Peptide and Protein Drugs," *Eur. J. Drug Metab. Pharmacokinet.*, 15(2), 95–102 (1990).

Sattentau et al., "The Human and Simian Immunodeficiency Viruses HIV–1, HIV–2 and SIV Interact with Similar Epitopes on Their Cellular Receptor, the CD4 Molecule," *AIDS*, 2(2), 101–105 (1988).

Schooley et al., "Recombinant Soluble CD4 Therapy in Patients with the Acquired Immunodeficiency Syndrome (AIDS) and AIDS–Related Complex," *Annals of Internal Medicine*, 112(4), 247–253 (1990).

Sherman et al., "The Protein Composition of the Photosynthetic Complexes from the Cyanobacterial Thylakoid Membrane," *The Cyanobacteria*, P. Fay et al., eds., Elsevier Science Publishers B.V. (Biomedical Division), 1987, pp. 1–33.

Shih et al., "Chimeric Human Immunodeficiency Virus Type 1/Type 2 Reverse Transcriptases Display Reversed Sensitivity to Nonnucleoside Analog Inhibitors," *Proc. Natl. Acad. Sci. USA*, 88, 9878–9882 (1991).

Siddiqui et al., "Nonparenteral Administration of Peptide and Protein Drugs," *CRC Crit. Rev. Therapeutic Drug Carrier Systems*, 3(3), 195–208 (1987).

Sivonen et al., "Three New Microcystins, Cyclic Heptapeptide Hepatotoxins, from Nostoc sp. Strain 152," *Chem. Res. Toxicol.*, 5, 464–469 (1992).

Sofer, in *Introduction to Genetic Engineering*, Butterworth–Heinemann: Stoneham, MA, 1991, pp. 1–21 and 103–126.

Suter et al., "Amino Acid Sequences of α–Allophycocyanin B from Synechococcus 6301 and *Mastigocladus laminosus," FEBS Letters*, 217(2), 279–282 (1987).

Swanson et al., "Characterization of Phycocyanin Produced by cpcE and cpcF Mutants and Identification of an Intergenic Suppressor of the Defect in Bilin Attachment," *Journal of Biological Chemistry*, 267(23), 16146–16154 (1992).

Taylor, "Building A Chemical Barrer to HIV–1 Transmission," *The Journal of NIH Research*, 6, 26–27 (1994).

Theiβ et al., "Iontophoresis—Is There a Future for Clinical Application?," *Meth. Find. Exp. Clin. Pharmacol.*, 13(5), 353–359 (1991).

Till et al., "HIV–Infected Cells Are Killed by rCD4–Ricin A Chain," *Science*, 242, 1166–1168 (1988).

Traunecker et al., "Highly efficient Neutralization of HIV with Recombinant CD4–Immunoglobulin Molecules," *Nature*, 339, 68–70 (1989).

van Hoogdalem et al., "Intestinal Drug Absorption Enhancement—An Overview," *Pharmac. Ther.*, 44, 407–443 (1989).

Verhoef et al., "Transport of Peptide and Protein Drugs Across Biological Membranes," *Eur. J. Drug Metab. Phartmacokinet.*, 15(2), 83–93 (1990).

Wallace ete al., "Stand and Deliver: Getting Peptide Drugs Into the Body," *Science*, 260, 912–913 (1993).

Weislow et al., "New Soluble–Formazan Assay for HIV–1 Cytopathic Effects: Application to High–Flux Screening of Synthetic and Natural Products for AIDS–Antiviral Activity," *Journal of the National Cancer Institute*, 81(8), 577–586 (1989).

White et al., "A TIBO Derivative, R82913, Is a Potent Inhibitor of HIV–1 Reverse Transcriptase with Heteropolymer Templates," *Antiviral Research*, 16, 257–266 (1991).

Wileman et al., "Soluble Asparaginase–Dextran Conjugates Show Increased Circulatory Persistence and Lowered Antigen Reactivity," *J. Pharm. Pharmacol.*, 38, 264–271 (1986).

Wunsch, E., "Peptide Factors as Pharmaceuticals: Criteria for Application," *Biopolymers*, 22, 493–505 (1983).

Bowie et al., "Deciphering the Message in Protein Sequences: Tolerance to Amino Acid Substitutions," *Science*, 247, 1306–1310 (1990).

Ngo et al., "Computational Complexity, Protein Structure Prediction, and the Levinthal Paradox," *The Protein Folding Problem and Tertiary Structure Prediction*, Merz et al., eds., Birkhauser, Boston, 492–495 (1994).

Orkin et al., *Report and Recommendations of the Panel to Assess the NIH Investment in Research on Gene Therapy.*

```
    FLAG Octapeptide

Asp Tyr Lys Asp Asp Asp Asp Lys Leu Gly Lys Phe Ser Gln Thr Cys Tyr Asn Ser Ala
                            Hind III
                    5'-CGA TCG AAG CTT GGT AAA TTC TCC CAG ACC TGC TAC AAC TCC GCT
                    3'-GCT AGC TTC GAA CCA TTT AAG AGG GTC TGG ACG ATG TTG AGG CGA
Ile Gln Gly Ser Val Leu Thr Ser Thr Cys Glu Arg Thr Asn Gly Gly Tyr Asn Thr Ser

ATC CAG GGT TCC GTT CTG ACC TCC ACC TGC GAA CGT ACC AAC GGT GGT TAC AAC ACC TCC
TAG GTC CCA AGG CAA GAC TGG AGG TGG ACG CTT GCA TGG TTG CCA CCA ATG TTG TGG AGG
Ser Ile Asp Leu Asn Ser Val Ile Glu Asn Val Asp Gly Ser Leu Lys Trp Gln Pro Ser

TCC ATC GAC CTG AAC TCC GTT ATC GAA AAC GTT GAC GGT TCC CTG AAA TGG CAG CCG TCC
AGG TAG CTG GAC TTG AGG CAA TAG CTT TTG CAA CTG CCA AGG GAC TTT ACC GTC GGC AGG
Asn Phe Ile Glu Thr Cys Arg Asn Thr Gln Leu Ala Gly Ser Ser Glu Leu Ala Ala Glu
                                          Bst XI
AAC TTC ATC GAA ACC TGC CGT AAC ACC CAG CTG GCT GGT TCC TCC GAA CTG GCT GCT GAA
TTG AAG TAG CTT TGG ACG GCA TTG TGG GTC GAC CGA CCA AGG AGG CTT GAC CGA CGA CTT
Cys Lys Thr Arg Ala Gln Gln Phe Val Ser Thr Lys Ile Asn Leu Asp Asp His Ile Ala
                     Esp I
TGC AAA ACC CGT GCT CAG CAG TTC GTT TCC ACC AAA ATC AAC CTG GAC GAC CAC ATC GCT
ACG TTT TGG GCA CGA GTC GTC AAG CAA AGG TGG TTT TAG TTG GAC CTG CTG GTG TAG CGA
Asn Ile Asp Gly Thr Leu Lys Tyr Glu
                                            Xho I
AAC ATC GAC GGT ACC CTG AAA TAC GAA TAA CTC GAG ATC GTA-3'
TTG TAG CTG CCA TGG GAC TTT ATG CTT ATT GAG CTC TAG CAT-5'
```

FIG. 2

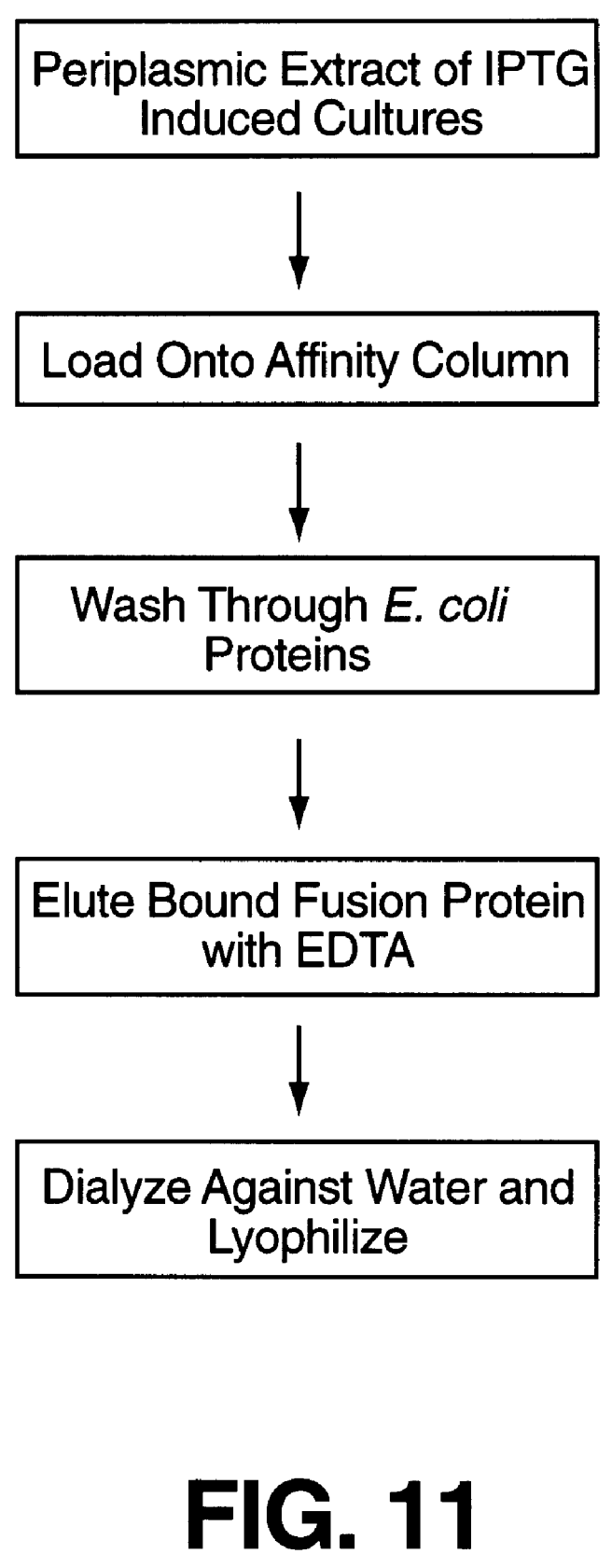

Periplasmic Extract of IPTG Induced Cultures

↓

Load Onto Affinity Column

↓

Wash Through *E. coli* Proteins

↓

Elute Bound Fusion Protein with EDTA

↓

Dialyze Against Water and Lyophilize

FIG. 11

METHODS OF OBTAINING ANTIVIRAL PROTEINS AND ANTIVIRAL PEPTIDES FROM *NOSTOC ELLIPSOSPORUM*

This is a divisional of copending application Ser. No. 08/429,965, filed on Apr. 27, 1995.

TECHNICAL FIELD OF THE INVENTION

This invention relates to antiviral proteins and peptides, collectively referred to as cyanovirins, and conjugates thereof, as well as methods of obtaining antiviral cyanovirins and conjugates thereof, compositions comprising cyanovirins and conjugates thereof, and methods of using cyanovirins and conjugates thereof in clinical applications, such as in antiviral therapy and prophylaxis.

BACKGROUND OF THE INVENTION

Acquired immune deficiency syndrome (AIDS) is a fatal disease, reported cases of which have increased dramatically within the past several years. The AIDS virus was first identified in 1983. It has been known by several names and acronyms. It is the third known T-lymphotropic virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV is used herein to refer to human immunodeficiency viruses generically.

HIV exerts profound cytopathic effects on the CD4$^+$ helper/inducer T-cells, thereby severely compromising the immune system. HIV infection also results in neurological deterioration and, ultimately, in death of infected individuals. Tens of millions of people are infected with HIV worldwide, and, without effective therapy, most of these are doomed to die. During the long latency, the period of time from initial infection to the appearance of symptoms, or death, due to AIDS, infected individuals spread the infection further, by sexual contacts, exchanges of contaminated needles during i.v. drug abuse, transfusions of blood or blood products, or maternal transfer of HIV to a fetus or newborn. Thus, there is not only an urgent need for effective therapeutic agents to inhibit the progression of HIV disease in individuals already infected, but also for methods of prevention of the spread of HIV infection from infected individuals to noninfected individuals. Indeed, the World Health Organization (WHO) has assigned an urgent international priority to the search for an effective anti-HIV prophylactic virucide to help curb the further expansion of the AIDS pandemic (Balter, *Science* 266, 1312–1313, 1994; Merson, *Science* 260, 1266–1268, 1993; Taylor, *J. NIH Res.* 6, 26–27, 1994; Rosenberg et al., *Sex. Transm. Dis.* 20, 41–44, 1993; and Rosenberg, *Am. J. Public Health* 82, 1473–1478, 1992).

The field of viral therapeutics has developed in response to the need for agents effective against retroviruses, especially HIV. There are many ways in which an agent can exhibit anti-retroviral activity (e.g., see DeClercq, *Adv. Virus Res.* 42, 1–55, 1993; DeClercq, *J. Acquir. Immun. Def. Synd.* 4, 207–218, 1991; and Mitsuya et al., *Science* 249, 1533–1544, 1990). Nucleoside derivatives, such as AZT, which inhibit the viral reverse transcriptase, are the only clinically active agents that are currently available commercially for anti-HIV therapy. Although very useful in some patients, the utility of AZT and related compounds is limited by toxicity and insufficient therapeutic indices for fully adequate therapy. Also, given the recent revelations about the true dynamics of HIV infection (Coffin, *Science* 267, 483–489, 1995; and Cohen, *Science* 267, 179, 1995), it is now increasingly apparent that agents acting as early as possible in the viral replicative cycle are needed to inhibit infection of newly produced, uninfected immune cells generated in the body in response to the virus-induced killing of infected cells. Also, it is essential to neutralize or inhibit new infectious virus produced by infected cells.

Therefore, new classes of antiviral agents, to be used alone or in combination with AZT and/or other available antiviral agents, are needed for effective antiviral therapy against-AIDS. New agents, which may be used to prevent HIV infection, are also important for prophylaxis. In both areas of need, the ideal new agent(s) would act as early as possible in the viral life cycle; be as virus-specific as possible (i.e., attack a molecular target specific to the virus but not the host); render the intact virus noninfectious; prevent the death or dysfunction of virus-infected cells; prevent further production of virus from infected cells; prevent spread of virus infection to uninfected cells; be highly potent and active against the broadest possible range of strains and isolates of HIV; be resistant to degradation under physiological and rigorous environmental conditions; and be readily and inexpensively produced on a large-scale basis.

Accordingly, it is an object of the present invention to provide antiviral proteins and peptides, and conjugates thereof, which possess the aforementioned particularly advantageous attributes.

It is a related object of the present invention to provide conjugates or chimeras containing an antiviral protein or peptide coupled to an effector molecule.

It is still another object of the present invention to provide a composition, in particular a pharmaceutical composition, which inhibits the growth or replication of a virus, such as a retrovirus, in particular a human immunodeficiency virus, specifically HIV-1 or HIV-2.

It is another object of the present invention to provide methods of obtaining an antiviral protein or peptide or conjugate thereof.

It is yet another object of the present invention to provide nucleic acid molecules, including recombinant vectors, encoding such antiviral proteins and peptides and conjugates thereof. A more specific object of the present invention is to provide a DNA coding sequence comprising SEQ ID NO:1.

It is another specific object of the present invention to provide a DNA coding sequence comprising SEQ ID NO:3.

Yet another object of the present invention is to provide a method of using an antiviral protein or peptide to target an effector molecule to virus and/or to virus-producing cells, specifically to retrovirus and/or to retrovirus-producing cells, more specifically to HIV and/or HIV-producing cells, and even more specifically to viral gp120 and/or cell-expressed gp120.

Still yet another object of the present invention is to provide a method of treating an animal, in particular a human, infected by a virus, such as a retrovirus, in particular a human immunodeficiency virus, specifically HIV-2 or HIV-2. A related object of the present invention is to provide a method of treating an animal, in particular a human, to prevent infection by a virus, such as a retrovirus, in particular a human immunodeficiency virus, specifically HIV-1 or HIV-2.

It is another related object of the present invention to provide a method of treating inanimate objects, such as medical and laboratory equipment and supplies, to prevent infection of an animal, in particular a human, by a virus, such as a retrovirus, in particular a human immunodeficiency virus, specifically HIV-1 or HIV-2. It is a further related object of the present invention to provide a method of treating injectable or infusible fluids, suspensions or solutions, such as blood or blood products, and tissues to prevent infection of an animal, in particular a human, by a virus, such as a retrovirus, in particular a human immunodeficiency virus, specifically HIV-1 or HIV-2.

These and other objects of the present invention, as well as additional inventive features, will become apparent from the description provided herein.

BRIEF SUMMARY OF THE INVENTION

The present invention provides antiviral agents, in particular antiviral proteins and peptides, collectively referred to as cyanovirins, and conjugates thereof, which are useful for antiviral therapy and prophylaxis. Cyanovirins and conjugates thereof inhibit the infectivity, cytopathicity and replication of a virus, in particular a retrovirus, specifically a human immunodeficiency virus, such as HIV-1 or HIV-2. Also provided are methods of obtaining a cyanovirin and a conjugate thereof. Nucleic acid molecules, including nucleic acid molecules of specified nucleotide sequence and recombinant vectors, encoding cyanovirins and conjugates thereof are also provided. The invention also provides a method of using a cyanovirin to target an effector molecule to a virus, such as a retrovirus, specifically HIV, and/or a virus-producing, such as a retrovirus-producing, specifically HIV-producing, cell, in particular viral gp120 and/or cell-express gp120. The present invention also provides a method of obtaining a substantially pure cyanovirin and a conjugate thereof. The cyanovirin or conjugate thereof can be used in a composition, such as a pharmaceutical composition, which can additionally comprise one or more other antiviral agents. The cyanovirin, conjugate, and composition thereof, alone or in combination with another antiviral agent, therefore, is useful in the therapeutic and prophylactic treatment of an animal, such as a human, infected or at risk for infection with a virus, particularly a retrovirus, specifically a human immunodeficiency virus, such as HIV-1 or HIV-2, and in the treatment of inanimate objects, such as medical and laboratory equipment and supplies, suspensions or solutions, such as blood and blood products, and tissues to prevent viral infection of an animal, such as a human.

BRIEF DESCRIPTION OF THE DRAWINGS

FIG. 2 shows an example of a DNA sequence encoding a synthetic cyanovirin gene (SEQ ID NOS.1–4).

FIG. 11 is a flowchart of the purification of recombinant cyanovirin proteins as described in Example 4.

DETAILED DESCRIPTION OF THE INVENTION AND PREFERRED EMBODIMENTS

Figure 1B:
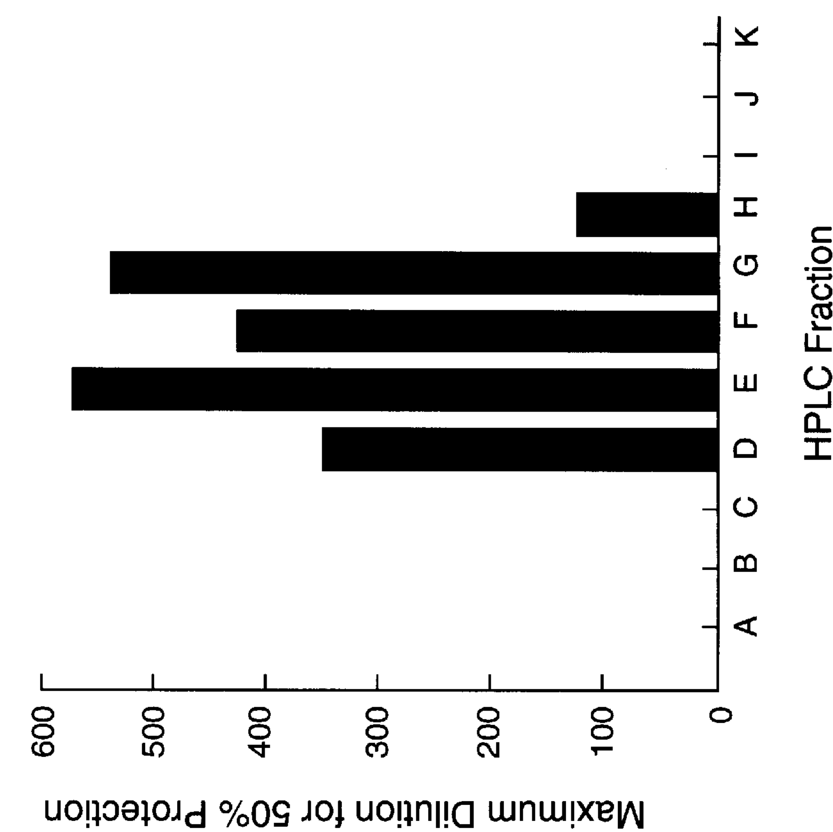
FIG. 1B is a bar graph of maximum dilution for 50% protection versus HPLC fraction, which illustrates the maximum dilution of each HPLC fraction that provided 50% protection from the cytopathic effects of HIV infection for the nonreduced cyanovirin HPLC fractions.

Infection of $CD4^+$ cells by HIV-1 and related primate immunodeficiency viruses begins with interaction of the respective viral envelope glycoproteins (generically termed "gp120") with the cell-surface receptor CD4, followed by fusion and entry (Sattentau, *AIDS* 2, 101–105, 1988; and Koenig et al., *PNAS USA* 86, 2443–2447, 1989). Productively infected, virus-producing cells express gp120 at the cell surface; interaction of gp120 of infected cells with CD4 on uninfected cells results in formation of dysfunctional multicellular syncytia and further spread of viral infection (Freed et al., *Bull. Inst. Pasteur* 88, 73, 1990). Thus, the gp120/CD4 interaction is a particularly attractive target for interruption of HIV infection and cytopathogenesis, either by prevention of initial virus-to-cell binding or by blockage of cell-to-cell fusion (Capon et al., *Ann. Rev. Immunol.* 9, 649–678, 1991). Virus-free or "soluble" gp120 shed from virus or from infected cells in vivo is also an important therapeutic target, since it may otherwise contribute to noninfectious immunopathogenic processes throughout the body, including the central nervous system (Capon et al., 1991, supra; and Lipton, *Nature* 367, 113–114, 1994). Much vaccine research has focused upon gp120; however, progress has been hampered by hypervariability of the gp120-neutralizing determinants, and consequent extreme strain-dependence of viral sensitivity to gp120-directed antibodies (Berzofsky, *J. Aca. Immun. Def. Synd.* 4, 451–459, 1991). Relatively little drug discovery and development research has focused specifically upon gp120. A notable exception is the considerable effort that has been devoted to truncated, recombinant "CD4" proteins ("soluble CD4" or "sCD4"), which bind gp120 and inhibit HIV infectivity in vitro (Capon et al., 1991, supra; Schooley et al., *Ann. Int. Med.* 112, 247–253, 1990; and Husson et al., *J. Pediatr.* 121, 627–633, 1992). However, clinical isolates, in contrast to laboratory strains of HIV, have proven highly resistant to neutralization by sCD4 (Orloff et al., *AIDS Res. Hum. Retrovir.* 11, 335–342, 1995; and Moore et al., *J. Virol.* 66, 235–243, 1992). Initial clinical trials of sCD4 (Schooley et al., 1990, supra; and Husson et al., 1992, supra), and of sCD4-coupled immunoglobulins (Langner et al., *Arch. Virol.* 130, 157–170, 1993), and likewise of sCD4-coupled toxins designed to bind and destroy virus-expressing cells (Davey et al., *J. Infect. Dis.* 170, 1180–1188, 1994; and Ramachandran et al., *J. Infect. Dis.* 170, 1009–1113, 1994), have been disappointing. Newer gene-therapy approaches to generating sCD4 directly in vivo (Morgan et al., *AIDS Res. Hum. Retrovir.* 10, 1507–1515, 1994) will likely suffer similar frustrations.

In view of the above, the principal overall objective of the present invention is to provide antiviral proteins, peptides and derivatives thereof, and broad medical uses thereof, including prophylactic and/or therapeutic applications against viruses, such as retroviruses, in particular a human immunodeficiency virus, specifically HIV-1 or HIV-2.

An initial observation, which led to the present invention, was antiviral activity in certain extracts from cultured cyanobacteria (blue-green algae) tested in an anti-HIV screen. The screen is one that was conceived in 1986 (by M. R. Boyd of the National Institutes of Health) and has been developed and operated at the U.S. National Cancer Institute (NCI) since 1988 (see Boyd, in *AIDS, Etiology, Diagnosis, Treatment and Prevention*, DeVita et al., eds., Philadelphia: Lippincott, 1988, pp. 305–317).

Cyanobacteria (blue-green algae) were specifically chosen for anti-HIV screening because they had been known to produce a wide variety of structurally unique and biologically active non-nitrogenous and amino acid-derived natural products (Faulkner, *Nat. Prod. Rep.* 11, 355–394, 1994; and Glombitza et al., in *Algal and Cyanobacterial Biotechnology*, Cresswell, R. C., et al. eds., 1989, pp. 211–218). These photosynthetic procaryotic organisms are significant producers of cyclic and linear peptides (molecular weight generally <3 kDa), which often exhibit hepatotoxic or antimicrobial properties (Okino et al., *Tetrahedron Lett.* 34, 501–504, 1993; Krishnamurthy et al., *PNAS USA* 86, 770–774, 1989; Sivonen et al., *Chem. Res. Toxicol.* 5, 464–469, 1992; Carter et al., *J. Org. Chem.* 49, 236–241, 1984; and Frankmolle et al., *J. Antibiot.* 45, 1451–1457, 1992). Sequencing studies of higher molecular weight cyanobacterial peptides and proteins have generally focused on those associated with primary metabolic processes or ones that can serve as phylogenetic markers (Suter et al., *FEBS Lett.* 217, 279–282, 1987; Rumbeli et al., *FEBS Lett.* 221, 1–2, 1987; Swanson et al., *J. Biol. Chem.* 267, 16146–16154, 1992; Michalowski et al., *Nucleic Acids Res.* 18, 2186, 1990; Sherman et al., in *The Cyanobacteria*, Fay et al., eds., Elsevier: New York, 1987, pp. 1–33; and Rogers, in *The Cyanobacteria*, Fay et al., eds., Elsevier: New York, 1987, pp. 35–67). In general, proteins with antiviral properties have not been associated with cyanobacterial sources.

The cyanobacterial extract leading to the present invention was among many thousands of different extracts initially selected randomly and tested blindly in the anti-HIV screen described above. A number of these extracts had been determined preliminarily to show anti-HIV activity in the NCI screen (Patterson et al., *J. Phycol.* 29, 125–130, 1993). From this group, an aqueous extract from *Nostoc ellipsosporum*, which had been prepared as described (Patterson, 1993, supra) and which showed an unusually high anti-HIV potency and in vitro "therapeutic index" in the NCI primary screen, was selected for detailed investigation. A specific bioassay-guided strategy was used to isolate and purify a homogenous protein highly active against HIV.

In the bioassay-guided strategy, initial selection of the extract for fractionation, as well as the decisions concerning the overall chemical isolation method to be applied, and the nature of the individual steps therein, were determined by interpretation of biological testing data. The anti-HIV screening assay (e.g., see Boyd, 1988, supra; Weislow et al., *J. Natl. Cancer Inst.* 81, 577–586, 1989), which was used to guide the isolation and purification process, measures the degree of protection of human T-lymphoblastoid cells from the cytopathic effects of HIV. Fractions of the extract of interest are prepared using a variety of chemical means and are tested blindly in the primary screen. Active fractions are separated further, and the resulting subfractions are likewise tested blindly in the screen. This process is repeated as many times as necessary in order to obtain the active compound(s), i.e., antiviral fraction(s) representing pure compound(s), which then can be subjected to detailed chemical analysis and structural elucidation.

Using this strategy, aqueous extracts of *Nostoc ellipsosporum* were shown to contain an antiviral protein. Accordingly, the present invention provides an isolated and purified antiviral protein, named cyanovirin-N, from *Nostoc ellipsosporum*. Herein the term "cyanovirin" is used generically to refer to a native cyanovirin or any related, functionally equivalent protein, peptide or derivative thereof. By definition, in this context, a related, functionally equivalent protein, peptide or derivative thereof a) contains a sequence of at least nine amino acids directly homologous with any subsequence of nine contiguous amino acids contained within a native cyanovirin, and, b) is capable of specifically binding to virus, more specifically a primate immunodeficiency virus, more specifically HIV-1, HIV-2 or SIV, or to an infected host cell expressing one or more viral antigen(s), more specifically an envelope glycoprotein, such as gp120, of the respective virus. Herein, the term "protein" refers to a sequence comprising 100 or more amino acids, whereas "peptide" refers to a sequence comprising less than 100 amino acids. Preferably, the protein, peptide or derivative thereof comprises an amino acid sequence that is substantially homologous to that of an antiviral protein from *Nostoc ellipsosporum*. By "substantially homologous" is meant sufficient homology to render the protein, peptide or derivative thereof antiviral, with antiviral activity characteristic of an antiviral protein isolated from *Nostoc ellipsosporum*. At least about 50% homology, preferably at least about 75% homology, and most preferably at least about 90% homology should exist. A cyanovirin conjugate comprises a cyanovirin coupled to one or more selected effector molecule(s), such as a toxin or immunological reagent. "Immunological reagent" will be used to refer to an antibody, an immunoglobulin, and an immunological recognition element. An immunological recognition element is an element, such as a peptide, e.g., the FLAG sequence of the recombinant cyanovirin-FLAG fusion protein, which facilitates, through immunological recognition, isolation and/or purification and/or analysis of the protein or peptide to which it is attached. A cyanovirin fusion protein is a type of cyanovirin conjugate, wherein a cyanovirin is coupled to one or more other protein(s) having any desired properties or effector functions, such as cytotoxic or immunological properties, or other desired properties, such as to facilitate isolation, purification or analysis of the fusion protein.

Accordingly, the present invention provides an isolated and purified protein encoded by a nucleic acid molecule comprising a sequence of SEQ ID NO:1, a nucleic acid molecule comprising a sequence of SEQ ID NO:3, a nucleic acid molecule encoding an amino acid sequence of SEQ ID NO:2, or a nucleic acid molecule encoding an amino acid sequence of SEQ ID NO:4. Preferably, the aforementioned nucleic acid molecules encode at least nine contiguous amino acids of the amino acid sequence of SEQ ID NO:2.

The present invention also provides a method of obtaining a cyanovirin from *Nostoc ellipsosporum*. Such a method comprises (a) identifying an extract of *Nostoc ellipsosporum* containing antiviral activity, (b) optionally removing high molecular weight biopolymers from the extract, (c) antiviral bioassay-guided fractionating the extract to obtain a crude extract of cyanovirin, and (d) purifying the crude extract by reverse-phase HPLC to obtain cyanovirin (see, also, Example 1). More specifically, the method involves the use of ethanol to remove high molecular weight biopolymers from the extract and the use of an anti-HIV bioassay to guide fractionation of the extract.

Cyanovirin-N, which was isolated and purified using the aforementioned method, was subjected to conventional procedures typically used to determine the amino acid sequence of a given pure protein. Thus, the cyanovirin was initially sequenced by N-terminal Edman degradation of intact protein and numerous overlapping peptide fragments generated by endoproteinase digestion. Amino acid analysis was in agreement with the deduced sequence. ESI mass spectrometry of reduced, HPLC-purified cyanovirin-N showed a molecular ion consistent with the calculated value. These studies indicated that cyanovirin-N from *Nostoc ellipsosporum* was comprised of a unique sequence of 101 amino acids having little or no significant homology to previously described proteins or transcription products of known nucleotide sequences. No more than eight contiguous amino acids from cyanovirin were found in any amino acid sequences from known proteins, nor were there any known proteins from any source containing greater than 13% sequence homology with cyanovirin-N. Given the chemically deduced amino acid sequence of cyanovirin-N, a corresponding recombinant cyanovirin-N (r-cyanovirin-N) was created and used to definitively establish that the deduced amino acid sequence was, indeed, active against virus, such as HIV (Boyd et al., 1995, supra; also, see Examples 2–5).

Accordingly, the present invention provides isolated and purified nucleic acid molecules and synthetic nucleic acid molecules, which comprise a coding sequence for a cyanovirin, such as an isolated and purified nucleic acid molecule comprising a sequence of SEQ ID NO:1, an isolated and purified nucleic acid molecule comprising a sequence of SEQ ID NO:3, an isolated and purified nucleic acid molecule encoding an amino acid sequence of SEQ ID NO:2, an isolated and purified nucleic acid molecule encoding an amino acid sequence of SEQ ID NO:4, and a nucleic acid molecule that is substantially homologous to any one or more of the aforementioned nucleic acid molecules. By "substantially homologous" is meant sufficient homology to render the protein, peptide or derivative thereof antiviral, with antiviral activity characteristic of an antiviral protein isolated from *Nostoc ellipsosporum*. At least about 50% homology, preferably at least about 75% homology, and most preferably at least about 90% homology should exist. More specifically, the present invention provides one of the aforementioned nucleic acid molecules, which comprises a nucleic acid sequence encoding at least nine contiguous amino acids of the amino acid sequence of SEQ ID NO:2.

Given the present disclosure, it will be apparent to one skilled in the art that a partial cyanovirin-N gene codon sequence will likely suffice to code for a fully functional, i.e., antiviral, such as anti-HIV, cyanovirin. A minimum essential DNA coding sequence(s) for a functional cyanovirin can readily be determined by one skilled in the art, for example, by synthesis and evaluation of sub-sequences comprising the native cyanovirin, and by site-directed mutagenesis studies of the cyanovirin-N DNA coding sequence.

Using an appropriate DNA coding sequence, a recombinant cyanovirin can be made by genetic engineering techniques (for general background see, e.g., Nicholl, in *An Introduction to Genetic Engineering*, Cambridge University Press: Cambridge, 1994, pp. 1–5 & 127–130; Steinberg et al., in *Recombinant DNA Technology Concepts and Biomedical Applications*, Prentice Hall: Englewood Cliffs, N.J., 1993, pp. 81–124 & 150–162; Sofer in *Introduction to Genetic Engineering*, Butterworth-Heinemann, Stoneham, Mass., 1991, pp. 1–21 & 103–126; Old et al., in *Principles of Gene Manipulation*, Blackwell Scientific Publishers: London, 1992, pp. 1–13 & 108–221; and Emtage, in *Delivery Systems for Peptide Drugs*, Davis et al., eds., Plenum Press: New York, 1986, pp. 23–33). For example, a *Nostoc ellipsosporum* gene or cDNA encoding a cyanovirin can be identified and subcloned. The gene or cDNA can then be incorporated into an appropriate expression vector and delivered into an appropriate protein-synthesizing organism (e.g., *E. coli, S. cerevisiae, P. pastoris*, or other bacterial, yeast, insect or mammalian cells), where the gene, under the control of an endogenous or exogenous promoter, can be appropriately transcribed and translated. Such expression vectors (including, but not limited to, phage, cosmid, viral, and plasmid vectors) are known to those skilled in the art, as are reagents and techniques appropriate for gene transfer (e.g., transfection, electroporation, transduction, microinjection, transformation, etc.). Subsequently, the recombinantly produced protein can be isolated and purified using standard techniques known in the art (e.g., chromatography, centrifugation, differential solubility, isoelectric focusing, etc.), and assayed for antiviral activity.

Alternatively, a native cyanovirin can be obtained from *Nostoc ellipsosporum* by non-recombinant methods (e.g., see Example 1 and above), and sequenced by conventional techniques. The sequence can then be used to synthesize the corresponding DNA, which can be subcloned into an appropriate expression vector and delivered into a protein-producing cell for en mass recombinant production of the desired protein.

In this regard, the present invention also provides a vector comprising a DNA sequence, e.g., a *Nostoc ellipsosporum* gene sequence for cyanovirin, a cDNA encoding a cyanovirin, or a synthetic DNA sequence encoding cyanovirin, a host cell comprising the vector, and a method of using such a host cell to produce a cyanovirin.

The DNA, whether isolated and purified or synthetic, or cDNA encoding a cyanovirin can encode for either the entire cyanovirin or a portion thereof. Where the DNA or cDNA does not comprise the entire coding sequence of the native cyanovirin, the DNA or cDNA can be subcloned as part of a gene fusion. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as at least some of the translational control sequences (i.e., the translational initiation codon) will be provided by the vector. In the case of a translational gene fusion, a chimeric protein will be produced.

Genes also can be constructed for specific fusion proteins containing a functional cyanovirin component plus a fusion component conferring additional desired attribute(s) to the composite protein. For example, a fusion sequence for a toxin or immunological reagent, as defined above, can be added to facilitate purification and analysis of the functional protein (e.g., such as the FLAG-cyanovirin-N fusion protein detailed within Examples 2–5).

Genes can be specifically constructed to code for fusion proteins, which contain a cyanovirin coupled to an effector protein, such as a toxin or immunological reagent, for specific targeting to viral-infected, e.g., HIV and/or HIV-infected, cells. In these instances, the cyanovirin moiety serves not only as a neutralizing agent but also as a targeting agent to direct the effector activities of these molecules selectively against a given virus, such as HIV. Thus, for example, a therapeutic agent can be obtained by combining the HIV-targeting function of a functional cyanovirin with a toxin aimed at neutralizing infectious virus and/or by destroying cells producing infectious virus, such as HIV. Similarly, a therapeutic agent can be obtained, which combines the viral-targeting function of a cyanovirin with the multivalency and effector functions of various immunoglobulin subclasses.

Similar rationales underlie extensive developmental therapeutic efforts exploiting the HIV gp120-targeting properties of sCD4. For example, sCD4-toxin conjugates have been prepared in which sCD4 is coupled to a Pseudomonas exotoxin component (Chaudhary et al., in *The Human Retrovirus*, Gallo et al., eds., Academic Press: San Diego, 1991, pp. 379–387; and Chaudhary et al., *Nature* 335, 369–372, 1988), or to a diphtheria toxin component (Aullo et al., *EMBO J.* 11, 575–583, 1992) or to a ricin A-chain component (Till et al., *Science* 242, 1166–1167, 1988). Likewise, sCD4-immunoglobulin conjugates have been prepared in attempts to decrease the rate of in vivo clearance of functional sCD4 activity, to enhance placental transfer, and to effect a targeted recruitment of immunological mechanisms of pathogen elimination, such as phagocytic engulfment and killing by antibody-dependent cell-mediated cytotoxicity, to kill and/or remove HIV-infected cells and virus (Capon et al., *Nature* 337, 525–531, 1989; Traunecker et al., *Nature* 339, 68–70, 1989; and Langner et al., 1993, supra). While such CD4-immunoglobulin conjugates (sometimes called “immunoadhesins”) have, indeed, shown advantageous pharmacokinetic and distributional attributes in vivo, and anti-HIV effects in vitro, clinical results have been discouraging (Schooley et al., 1990, supra; Husson et al., 1992, supra; and Langner et al., 1993, supra). This is not surprising since clinical isolates of HIV, as opposed to laboratory strains, are highly resistant to binding and neutralization by sCD4 (Orloff et al., 1995, supra; and Moore et al., 1992, supra). Therefore, the extraordinarily broad targeting properties of a functional cyanovirin to viruses, e.g., primate retroviruses, in general, and clinical and laboratory strains, in particular (Boyd et al., 1995, supra; and Gustafson et al., 1995, supra), can be especially advantageous for combining with toxins, immunoglobulins and other selected effector proteins.

Viral-targeted conjugates can be prepared either by genetic engineering techniques (see, for example, Chaudhary et al., 1988, supra) or by chemical coupling of the targeting component with an effector component. The most feasible or appropriate technique to be used to construct a given cyanovirin conjugate or fusion protein will be selected based upon consideration of the characteristics of the particular effector molecule selected for coupling to a cyanovirin. For example, with a selected non-proteinaceous effector molecule, chemical coupling, rather than genetic engineering techniques, may be the only feasible option for creating the desired cyanovirin conjugate.

Accordingly, the present invention also provides nucleic acid molecules encoding cyanovirin fusion proteins. In particular, the present invention provides a nucleic acid molecule comprising SEQ ID NO:3 and substantially homologous sequences thereof. Also provided is a vector comprising a nucleic acid sequence encoding a cyanovirin fusion protein and a method of obtaining a cyanovirin fusion protein by expression of the vector encoding a cyanovirin fusion protein in a protein-synthesizing organism as described above. Accordingly, cyanovirin fusion proteins are also provided.

In view of the above, the present invention further provides an isolated and purified nucleic acid molecule, which comprises a cyanovirin coding sequence, such as one of the aforementioned nucleic acids, namely a nucleic acid molecule encoding an amino acid sequence of SEQ ID NO:2, a nucleic acid molecule encoding an amino acid sequence of SEQ ID NO:4, a nucleic acid molecule comprising a sequence of SEQ ID NO:1, or a nucleic acid molecule comprising a sequence of SEQ ID NO:3, coupled to a second nucleic acid encoding an effector protein. The first nucleic acid preferably comprises a nucleic acid sequence encoding at least nine contiguous amino acids of the amino acid sequence of SEQ ID NO:2, which encodes a functional cyanovirin, and the second nucleic acid preferably encodes an effector protein, such as a toxin or immunological reagent as described above.

Accordingly, the present invention also further provides an isolated and purified protein encoded by a nucleic acid molecule comprising a sequence of SEQ ID NO:1, a nucleic acid molecule comprising a sequence of SEQ ID NO:3, a nucleic acid molecule encoding an amino acid sequence of SEQ ID NO:2, or a nucleic acid molecule encoding an amino acid sequence of SEQ ID NO:4. Preferably, the aforementioned nucleic acid molecules encode at least nine contiguous amino acids of the amino acid sequence of SEQ ID NO:2 coupled to an effector molecule, such as a toxin or immunological reagent as described above. Preferably, the effector molecule targets a virus, more preferably HIV, and, most preferably glycoprotein gp120. The coupling can be effected at the DNA level or by chemical coupling as described above. For example, a cyanovirin-effector protein conjugate of the present invention can be obtained by (a)

selecting a desired effector protein or peptide; (b) synthesizing a composite DNA coding sequence comprising a first DNA coding sequence comprising one of the aforementioned nucleic acid sequences, which codes for a functional cyanovirin, coupled to a second DNA coding sequence for an effector protein or peptide, e.g., a toxin or immunological reagent; (c) expressing said composite DNA coding sequence in an appropriate protein-synthesizing organism; and (d) purifying the desired fusion protein or peptide to substantially pure form. Alternatively, a cyanovirin-effector molecule conjugate of the present invention can be obtained by (a) selecting a desired effector molecule and a cyanovirin or cyanovirin fusion protein; (b) chemically coupling the cyanovirin or cyanovirin fusion protein to the effector molecule; and (c) purifying the desired cyanovirin-effector molecule conjugate to substantially pure form.

Conjugates containing a functional cyanovirin coupled to a desired effector component, such as a toxin, immunological reagent, or other functional reagent, can be designed even more specifically to exploit the unique gp120-targeting properties of cyanovirins. Example 6 reveals novel gp120-directed effects of cyanovirins. Additional insights were gained from solid-phase ELISA experiments (Boyd et al., 1995, supra). Both C-terminal gp120-epitope-specific capture or CD4-receptor capture of gp120, when detected either with polyclonal HIV-1-Ig or with mouse MAb to the immunodominant, third hypervariable (V3) epitope (Matsushita et al., *J. Virol.* 62, 2107–2114, 1988), were strikingly inhibited by cyanovirin. Generally, engagement of the CD4 receptor does not interfere with antibody recognition of the V3 epitope, and vice versa (Moore et al., *AIDS Res. Hum. Retrovir.* 4, 369–379, 1988; and Matsushita et al., 1988, supra). However, cyanovirin apparently is capable of more global conformational effects on gp120, as evidenced by loss of immunoreactivity at multiple, distinct, non-overlapping epitopes. The range of antiviral activity (Boyd et al., 1995, supra) of cyanovirin against diverse $CD4^+$-tropic immunodeficiency virus strains in various target cells is remarkable; all tested strains of HIV-1, HIV-2 and SIV were similarly sensitive to cyanovirin; clinical isolates and laboratory strains showed essentially equivalent sensitivity. Cocultivation of chronically infected and uninfected CEM-SS cells with cyanovirin did not inhibit viral replication, but did cause a concentration-dependent inhibition of cell-to-cell fusion and virus transmission; similar results from binding and fusion inhibition assays employing HeLa-CD4-LTR-β-galactosidase cells were consistent with cyanovirin inhibition of virus-cell and/or cell-cell binding.

The anti-viral, e.g., anti-HIV, activity of the cyanovirins and conjugates thereof of the present invention can be further demonstrated in a series of interrelated in vitro antiviral assays (Gulakowski et al., *J. Virol. Methods* 33, 87–100, 1991), which accurately predict for antiviral activity in humans. These assays measure the ability of compounds to prevent the replication of HIV and/or the cytopathic effects of HIV on human target cells. These measurements directly correlate with the pathogenesis of HIV-induced disease in vivo. The results of the analysis of the antiviral activity of cyanovirins or conjugates, as set forth in Example 5 and as illustrated in FIGS. 5A–6D, are believed to predict accurately the antiviral activity of these products in vivo in humans and, therefore, establish the utility of the present invention. Furthermore, since the present invention also provides methods of ex vivo use of cyanovirins and conjugates (e.g., see results set forth in Example 5, and in FIGS. 5A–6D), the utility of cyanovirins and conjugates thereof is even more certain.

The cyanovirins and conjugates thereof of the present invention can be shown to inhibit a virus, specifically a retrovirus, such as the human immunodeficiency virus, i.e., HIV-1 or HIV-2. The cyanovirins and conjugates of the present invention could be used to inhibit other retroviruses as well as other viruses. Examples of viruses that may be treated in accordance with the present invention include, but are not limited to, Type C and Type D retroviruses, HTLV-1, HTLV-2, HIV, FLV, SIV, MLV, BLV, BIV, equine infectious virus, anemia virus, avian sarcoma viruses, such as Rous sarcoma virus (RSV), hepatitis type A, B, non-A and non-B viruses, arboviruses, varicella viruses, measles, mumps and rubella viruses.

Cyanovirins and conjugates thereof collectively comprise proteins and peptides, and, as such, are particularly susceptible to hydrolysis of amide bonds (e.g., catalyzed by peptidases) and disruption of essential disulfide bonds or formation of inactivating or unwanted disulfide linkages (Carone et al., *J. Lab. Clin. Med.* 100, 1–14, 1982). There are various ways to alter molecular structure, if necessary, to provide enhanced stability to the cyanovirin or conjugate thereof (Wunsch, *Biopolymers* 22, 493–505, 1983; and Samanen, in *Polymeric Materials in Medication*, Gebelein et al., eds., Plenum Press: New York, 1985, pp. 227–242), which may be essential for preparation and use of pharmaceutical compositions containing cyanovirins or conjugates thereof for therapeutic or prophylactic applications against viruses, e.g., HIV. Possible options for useful chemical modifications of a cyanovirin or conjugate include, but are not limited to, the following (adapted from Samanen, J. M., 1985, supra): (a) olefin substitution, (b) carbonyl reduction, (c) D-amino acid substitution, (d) N α-methyl substitution, (e) C α-methyl substitution, (f) C α-C'-methylene insertion, (g) dehydro amino acid insertion, (h) retro-inverso modification, (i) N-terminal to C-terminal cyclization, and (j) thiomethylene modification. Cyanovirins and conjugates thereof also can be modified by covalent attachment of carbohydrate and polyoxyethylene derivatives, which are expected to enhance stability and resistance to proteolysis (Abuchowski et al., in *Enzymes as Drugs*, Holcenberg et al., eds., John Wiley: New York, 1981, pp. 367–378).

Other important general considerations for design of delivery strategy systems and compositions, and for routes of administration, for protein and peptide drugs, such as cyanovirins and conjugates thereof (Eppstein, *CRC Crit. Rev. Therapeutic Drug Carrier Systems* 5, 99–139, 1988; Siddiqui et al., *CRC Crit. Rev. Therapeutic Drug Carrier Systems* 3, 195–208, 1987); Banga et al., *Int. J. Pharmaceutics* 48, 15–50, 1988; Sanders, *Eur. J. Drug Metab. Pharmacokinetics* 15, 95–102, 1990; and Verhoef, *Eur. J. Drug Metab. Pharmacokinetics* 15, 83–93, 1990), also apply. The appropriate delivery system for a given cyanovirin or conjugate thereof will depend upon its particular nature, the particular clinical application, and the site of drug action. As with any protein or peptide drug, oral delivery of a cyanovirin or a conjugate thereof will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it will be necessary to use an absorption-enhancing agent in combination with a given cyanovirin or conjugate thereof. A wide variety of absorption-enhancing agents have been investigated and/or applied in combination with protein and peptide drugs for oral delivery and for delivery by other routes (Verhoef, 1990, supra; van Hoogdalem, *Pharmac. Ther.* 44, 407–443, 1989; Davis, *J. Pharm. Pharmacol.* 44(Suppl. 1), 186–190, 1992). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides and diglycerides, (e) non-surfactants, such as unsaturated cyclic ureas, (f) saponins, (g) cyclodextrins, and (h) phospholipids.

Other approaches to enhancing oral delivery of protein and peptide drugs, such as the cyanovirins and conjugates thereof, can include aforementioned chemical modifications to enhance stability to gastrointestinal enzymes and/or increased lipophilicity. Alternatively, or in addition, the protein or peptide drug can be administered in combination with other drugs or substances, which directly inhibit proteases and/or other potential sources of enzymatic degradation of proteins and peptides. Yet another alternative approach to prevent or delay gastrointestinal absorption of protein or peptide drugs, such as cyanovirins or conjugates, is to incorporate them into a delivery system that is designed to protect the protein or peptide from contact with the proteolytic enzymes in the intestinal lumen and to release the intact protein or peptide only upon reaching an area favorable for its absorption. A more specific example of this strategy is the use of biodegradable microcapsules or microspheres, both to protect vulnerable drugs from degradation, as well as to effect a prolonged release of active drug (Deasy, in *Microencapsulation and Related Processes*, Swarbrick, ed., Marcell Dekker, Inc.: New York, 1984, pp. 1–60, 88–89, 208–211). Microcapsules also can provide a useful way to effect a prolonged delivery of a protein and peptide drug, such as a cyanovirin or conjugate thereof, after injection (Maulding, *J. Controlled Release* 6, 167–176, 1987).

Given the aforementioned potential complexities of successful oral delivery of a protein or peptide drug, it is fortunate that there are numerous other potential routes of delivery of a protein or peptide drug, such as a cyanovirin or conjugate thereof. These routes include intravenous, intraarterial, intrathecal, intracisternal, buccal, rectal, nasal, pulmonary, transdermal, vaginal, ocular, and the like (Eppstein, 1988, sutra; Siddiqui et al., 1987, supra; Banga et al., 1988, supra; Sanders, 1990, sutra; Verhoef, 1990, sutra; Barry, in *Delivery Systems for Peptide Drugs*, Davis et al., eds., Plenum Press: New York, 1986, pp. 265–275; and Patton et al., *Adv. Drug Delivery Rev.* 8, 179–196, 1992). With any of these routes, or, indeed, with any other route of administration or application, a protein or peptide drug, such as a cyanovirin or conjugate thereof, may initiate an immunogenic reaction. In such situations it may be necessary to modify the molecule in order to mask immunogenic groups. It also can be possible to protect against undesired immune responses by judicious choice of method of formulation and/or administration. For example, site-specific delivery can be employed, as well as masking of recognition sites from the immune system by use or attachment of a so-called tolerogen, such as polyethylene glycol, dextran, albumin, and the like (Abuchowski et al., 1981, supra; Abuchowski et al., *J. Biol. Chem.* 252, 3578–3581, 1977; Lisi et al., *J. Appl. Biochem.* 4, 19–33, 1982; and Wileman et al., *J. Pharm. Pharmacol.* 38, 264–271, 1986). Such modifications also can have advantageous effects on stability and half-life both in vivo and ex vivo. Other strategies to avoid untoward immune reactions can also include the induction of tolerance by administration initially of only low doses. In any event, it will be apparent from the present disclosure to one skilled in the art that for any particular desired medical application or use of a cyanovirin or conjugate thereof, the skilled artisan can select from any of a wide variety of possible compositions, routes of administration, or sites of application, what is advantageous.

Accordingly, the antiviral cyanovirins and conjugates thereof of the present invention can be formulated into various compositions for use either in therapeutic treatment methods for infected individuals, or in prophylactic methods against viral, e.g., HIV, infection of uninfected individuals.

The present invention also provides a pharmaceutical composition, which comprises an antiviral effective amount of an isolated and purified cyanovirin or cyanovirin conjugate and a pharmaceutically acceptable carrier. The composition can further comprise an antiviral effective amount of at least one additional antiviral compound other than a cyanovirin or conjugate thereof. Suitable antiviral compounds include AZT, ddI, ddC, gancyclovir, fluorinated dideoxynucleosides, nevirapine, R82913, Ro 31–8959, BI-RJ-70, acyclovir, α-interferon, recombinant sCD4, michellamines, calanolides, nonoxynol-9, gossypol and derivatives thereof, and gramicidin. The cyanovirin used in the pharmaceutical composition can be isolated and purified from nature or genetically engineered. Similarly, the cyanovirin conjugate can be genetically engineered or chemically coupled.

The present inventive compositions can be used to treat a virally infected animal, such as a human. The compositions of the present invention are particularly useful in inhibiting the growth or replication of a virus, such as a retrovirus, in particular a human immunodeficiency virus, specifically HIV-1 and HIV-2. The compositions are useful in the therapeutic or prophylactic treatment of animals, such as humans, who are infected with a virus or who are at risk for viral infection, respectively. The compositions also can be used to treat objects or materials, such as medical equipment, supplies, or fluids, including biological fluids, such as blood, blood products, and tissues, to prevent viral infection of an animal, such as a human. Such compositions also are useful to prevent sexual transmission of viral infections, e.g., HIV, which is the primary way in which the world's AIDS cases are contracted (Merson, 1993, supra).

Potential virucides used or being considered for use against sexual transmission of HIV are very limited; present agents in this category include nonoxynol-9 (Bird, *AIDS* 5, 791–796, 1991), gossypol and derivatives (Polsky et al., *Contraception* 39, 579–587, 1989; Lin, *Antimicrob. Agents Chemother.* 33, 2149–2151, 1989; and Royer, *Pharmacol. Res.* 24, 407–412, 1991), and gramicidin (Bourinbair, *Life Sci./Pharmacol. Lett.* 54, PL5–9, 1994; and Bourinbair et al., *Contraception* 49, 131–137, 1994). The method of prevention of sexual transmission of viral infection, e.g., HIV infection, in accordance with the present invention comprises vaginal, rectal, oral, penile or other topical treatment with an antiviral effective amount of a cyanovirin and/or cyanovirin conjugate, alone or in combination with another antiviral compound as described above.

Compositions for use in the prophylactic or therapeutic treatment methods of the present invention comprise one or more cyanovirin(s) or conjugate(s) thereof and a pharmaceutically acceptable carrier. Pharmaceutically acceptable carriers are well-known to those who are skilled in the art, as are suitable methods of administration. The choice of carrier will be determined in part by the particular cyanovirin or conjugate thereof, as well as by the particular method used to administer the composition.

One skilled in the art will appreciate that various routes of administering a drug are available, and, although more than one route may be used to administer a particular drug, a particular route may provide a more immediate and more effective reaction than another route. Furthermore, one skilled in the art will appreciate that the particular pharmaceutical carrier employed will depend, in part, upon the particular cyanovirin or conjugate thereof employed, and the chosen route of administration. Accordingly, there is a wide variety of suitable formulations of the composition of the present invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al., *Science* 260, 912–915, 1993).

The cyanovirins or conjugates thereof, alone or in combination with other antiviral compounds, can be made into aerosol formulations to be administered via inhalation. These aerosol formulations can be placed into pressurized acceptable propellants, such as dichlorodifluoromethane, propane, nitrogen and the like.

The cyanovirins or conjugates thereof, alone or in combinations with other antiviral compounds or absorption modulators, can be made into suitable formulations for transdermal application and absorption (Wallace et al., 1993, supra). Transdermal electroporation or iontophoresis also can be used to promote and/or control the systemic delivery of the compounds and/or compositions of the present invention through the skin (e.g., see Theiss et al., *Meth. Find. Exp. Clin. Pharmacol.* 13, 353–359, 1991).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels and the like containing, in addition to the active ingredient, such carriers as are known in the art.

Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient, such carriers as are known in the art to be appropriate. Similarly, the active ingredient can be combined with a lubricant as a coating on a condom.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations comprising a cyanovirin or cyanovirin conjugate suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations. Preferably, the cyanovirin is produced by recombinant DNA technology. The cyanovirin conjugate can be produced by recombinant DNA technology or by chemical coupling of a cyanovirin with an effector molecule as described above. Similarly, formulations suitable for ex vivo virucidal sterilization of blood, blood products, sperm, or other bodily products or tissues, or any other solution, suspension, emulsion or any other material which can be administered to a patient in a medical procedure, can be selected or adapted as appropriate by one skilled in the art, from any of the aforementioned compositions or formulations. However, suitable formulations for such ex vivo applications or for virucidal treatment of inanimate objects are by no means limited to any of the aforementioned formulations or compositions. One skilled in the art will appreciate that a suitable or appropriate formulation can be selected, adapted or developed based upon the particular application at hand.

For ex vivo uses, such as virucidal treatments of inanimate objects or materials, blood or blood products, or tissues, the amount of cyanovirin, or conjugate or composition thereof, to be employed should be sufficient that any virus or virus-producing cells present will be rendered noninfectious or will be destroyed. For example, for HIV, this would require that the virus and/or the virus-producing cells be exposed to concentrations of cyanovirin-N in the range of 0.1–1000 nM. Similar considerations apply to in vivo applications. Therefore, the designation of "antiviral effective amount" is used generally to describe the amount of a particular cyanovirin, conjugate or composition thereof required for antiviral efficacy in any given application.

For in vivo uses, the dose of a cyanovirin, or conjugate or composition thereof, administered to an animal, particularly a human, in the context of the present invention should be sufficient to effect a prophylactic or therapeutic response in the individual over a reasonable time frame. The dose used to achieve a desired antiviral concentration in vivo (e.g., 0.1–1000 nM) will be determined by the potency of the particular cyanovirin or conjugate employed, the severity of the disease state of infected individuals, as well as, in the case of systemic administration, the body weight and age of the infected individual. The size of the dose also will be determined by the existence of any adverse side effects that may accompany the particular cyanovirin, or conjugate or composition thereof, employed. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a cyanovirin or conjugate thereof, alone or in combination with other antiviral agents, calculated in an amount sufficient to produce the desired effect in association with a pharmaceutically acceptable diluent, carrier, or vehicle.

The specifications for the unit dosage forms of the present invention depend on the particular cyanovirin, or conjugate or composition thereof, employed and the effect to be achieved, as well as the pharmacodynamics associated with each cyanovirin, or conjugate or composition thereof, in the host. The dose administered should be an "antiviral effective amount" or an amount necessary to achieve an "effective level" in the individual patient.

Since the "effective level" is used as the preferred endpoint for dosing, the actual dose and schedule can vary, depending upon interindividual differences in pharmacokinetics, drug distribution, and metabolism. The "effective level" can be defined, for example, as the blood or tissue level (e.g., 0.1–1000 nM) desired in the patient that corresponds to a concentration of one or more cyanovirin or conjugate thereof, which inhibits a virus, such as HIV, in an assay known to predict for clinical antiviral activity of chemical compounds and biological agents. The "effective level" for agents of the present invention also can vary when the cyanovirin, or conjugate or composition thereof, is used in combination with AZT or other known antiviral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effector concentration" of the compounds of the present invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it can be desirable to utilize a "mega-dosing" regimen, wherein a large dose of the cyanovirin or conjugate thereof is administered, time is allowed for the drug to act, and then a suitable reagent is administered to the individual to inactivate the drug.

The pharmaceutical composition can contain other pharmaceuticals, in conjunction with the cyanovirin or conjugate thereof, when used to therapeutically treat a viral infection, such as that which results in AIDS. Representative examples of these additional pharmaceuticals include antiviral compounds, virucides, immunomodulators, immunostimulants, antibiotics and absorption enhancers. Exemplary antiviral compounds include AZT, ddI, ddC, gancylclovir, fluorinated dideoxynucleosides, nonnucleoside analog compounds, such as nevirapine (Shih et al., *PNAS* 88, 9878–9882, 1991), TIBO derivatives, such as R82913 (White et al., *Antiviral Res.* 16, 257–266, 1991), BI-RJ-70 (Merigan, *Am. J. Med.* 90 (Suppl.4A), 8S-17S, 1991), michellamines (Boyd et al., *J. Med. Chem.* 37, 1740–1745, 1994) and calanolides (Kashman et al., *J. Med. Chem.* 35, 2735–2743, 1992), nonoxynol-9, gossypol and derivatives, and gramicidin (Bourinbair et al., 1994, supra). Exemplary immunomodulators and immunostimulants include various interleukins, sCD4, cytokines, antibody preparations, blood transfusions, and cell transfusions. Exemplary antibiotics include antifungal agents, antibacterial agents, and anti-*Pneumocystitis carnii* agents. Exemplary absorption enhancers include bile salts and other surfactants, saponins, cyclodextrins, and phospholipids (Davis, 1992, supra).

Administration of a cyanovirin or conjugate thereof with other anti-retroviral agents and particularly with known RT inhibitors, such as ddC, AZT, ddI, ddA, or other inhibitors that act against other HIV proteins, such as anti-TAT agents, is expected to inhibit most or all replicative stages of the viral life cycle. The dosages of ddC and AZT used in AIDS or ARC patients have been published. A virustatic range of ddC is generally between 0.05 $\mu$M to 1.0 $\mu$M. A range of about 0.005–0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently, 0.01 mg/kg body weight ddC given every 8 hrs is preferred. When given in combined therapy, the other antiviral compound, for example, can be given at the same time as the cyanovirin or conjugate thereof or the dosing can be staggered as desired. The two drugs also can be combined in a composition. Doses of each can be less when used in combination than when either is used alone.

It will also be appreciated by one skilled in the art that a DNA sequence of a cyanovirin or conjugate thereof of the present invention can be inserted ex vivo into mammalian cells previously removed from a given animal, in particular a human, host. Such cells can be employed to express the corresponding cyanovirin or conjugate in vivo after reintroduction into the host. Feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4 (Morgan et al., 1994, supra). It is also possible that, as an alternative to ex vivo insertion of the DNA sequences of the present invention, such sequences can be inserted into cells directly in vivo, such as by use of an appropriate viral vector. Such cells transfected in vivo are expected to produce antiviral amounts of cyanovirin or a conjugate thereof directly in vivo.

The present inventive cyanovirins, conjugates, compositions and methods are further described in the context of the following examples. These examples serve to illustrate further the present invention and are not intended to limit the scope of the invention.

EXAMPLES

Example 1

This example shows details of anti-HIV bioassay-guided isolation and elucidation of pure cyanovirin from aqueous extracts of the cultured cyanobacterium, *Nostoc ellipsosporum.*

The method described in Weislow et al. (1989, supra) was used to monitor and direct the isolation and purification process. Cyanobacterial culture conditions, media and classification were as described previously (Patterson, *J. Phycol.* 27, 530–536, 1991). Briefly, the cellular mass from a unialgal strain of *Nostoc ellipsosporum* (culture Q68D170) was harvested by filtration, freeze-dried and extracted with MeOH—$CH_2Cl_2$ (1:1) followed by $H_2O$. Bioassay indicated that only the $H_2O$ extract contained HIV-inhibitory activity. A solution of the aqueous extract (30 mg/ml) was treated by addition of an equal volume of ethanol (EtOH). The resulting 1:1 $H_2O$-EtOH solution was kept at −20° C. for 15 hrs. Then, the solution was centrifuged to remove precipitated materials (presumably, high molecular weight biopolymers). The resulting HIV-inhibitory supernatant was evaporated, then fractionated by reverse-phase vacuum-liquid chromatography (Coll et al., *J. Nat. Prod.* 49, 934–936, 1986;. and Pelletier et al., *J. Nat. Prod.* 49, 892–900, 1986) on wide-pore $C_4$ packing (300 Å, BakerBond WP-$C_4$), and eluted with increasing concentrations of methanol (MeOH) in $H_2O$. Anti-HIV activity was concentrated in the material eluted with MeOH—$H_2O$ (2:1). SDS-PAGE analysis of this fraction showed one main protein band, with a relative molecular mass (Mr) of approximately 10 kDa. Final purification was achieved by repeated reverse-phase HPLC on 1.9×15 cm μBondapak $C_{18}$ (Waters Associates) columns eluted with a gradient of increasing concentration of acetonitrile in $H_2O$. The mobile phase contained 0.05% (v/v) TFA, pH=2. Eluted proteins and peptides were detected by UV absorption at 206, 280 and 294 nm with a rapid spectral detector (Pharmacia LKB model 2140). Individual fractions were collected, pooled based on the UV chromatogram, and lyophilized. Pooled HPLC fractions were subjected to SDS-PAGE under reducing conditions (Laemmli, *Nature* 227, 680–685, 1970), conventional amino acid analysis, and testing for anti-HIV activity.

Figure 1A:
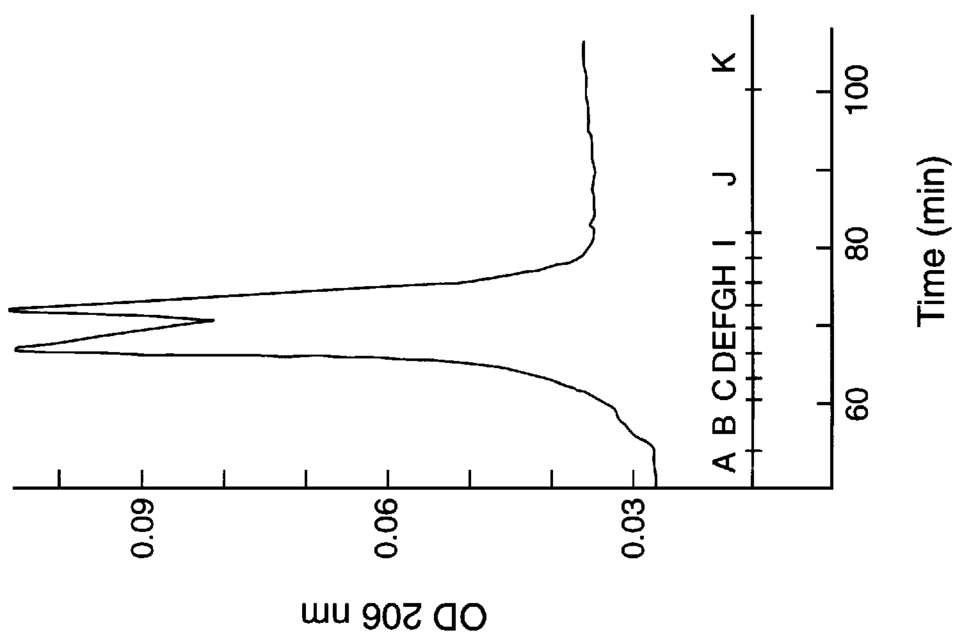
FIG. 1A is a graph of OD 206 nm versus time (min), which represents an HPLC chromatogram of nonreduced cyanovirin.
Figure 1D:
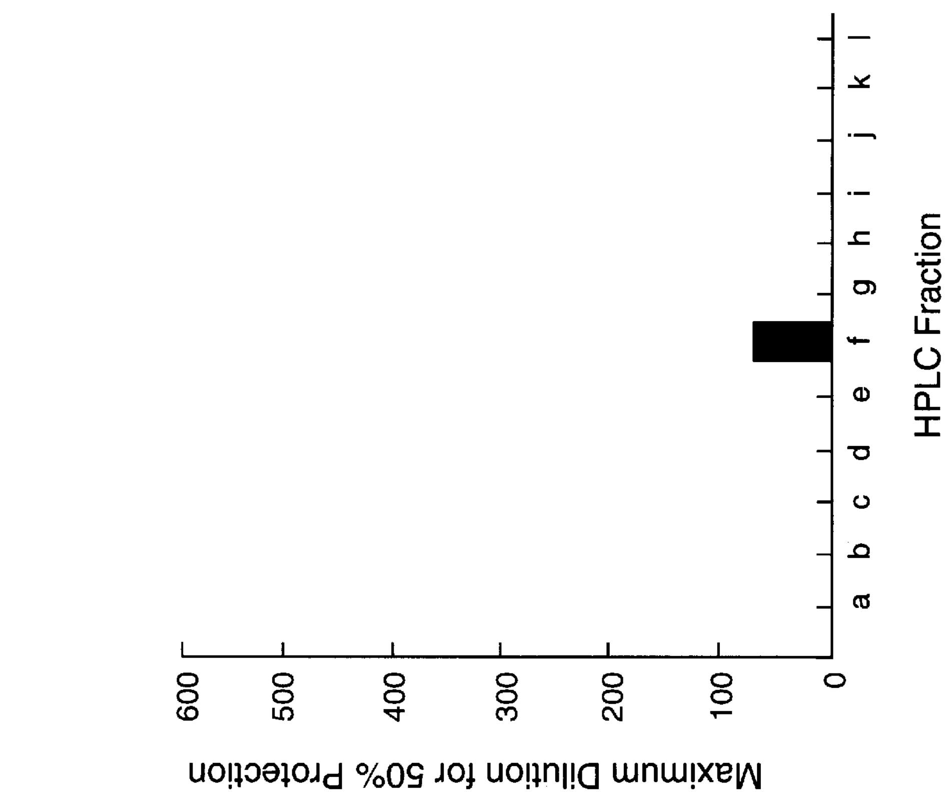
FIG. 1D is a bar graph of maximum dilution for 50% protection versus HPLC dilution, which illustrates the maximum dilution of each fraction that provided 50% protection from the cytopathic effects of HIV infection for the reduced cyanovirin HPLC fractions.
Figure 1C:
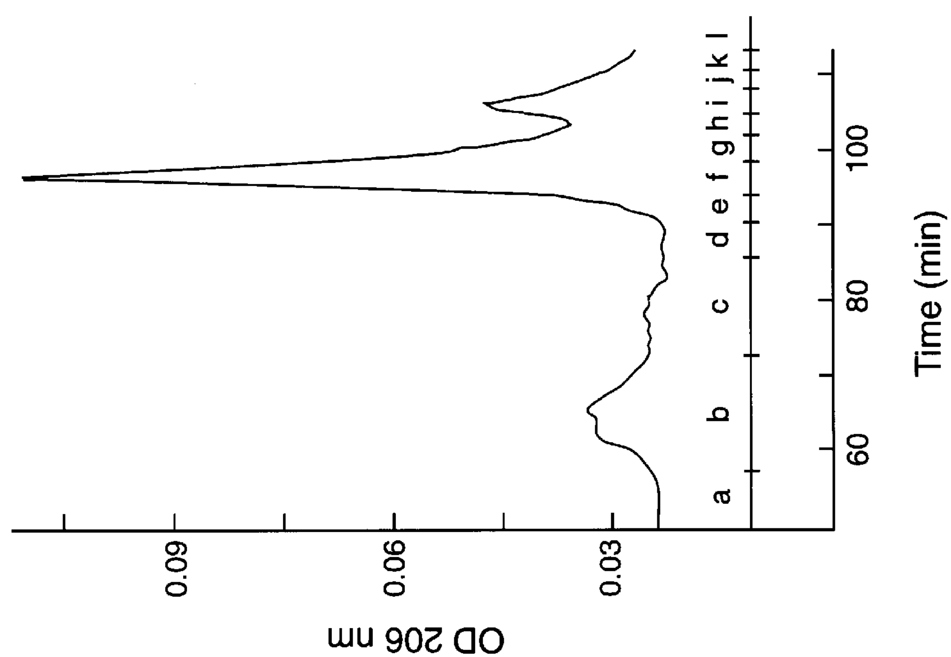
FIG. 1C is a graph of OD 206 nm versus time (min), which represents an HPLC chromatogram of reduced cyanovirin.

FIG. 1A is a graph of OD 206 nm versus time (min), which shows the μBondapak $C_{18}$ HPLC chromatogram of nonreduced cyanovirin eluted with a linear $CH_3CN/H_2O$ gradient (buffered with 0.05% TFA) from 28–38% $CH_3CN$. FIG. 1C is a graph of OD 206 nm versus time (min), which shows the chromatogram of cyanovirin that was first reduced with β-mercaptoethanol and then separated under identical HPLC conditions. HPLC fractions from the two runs were collected as indicated. 10% aliquots of each fraction were lyophilized, made up in 100 μl 3:1 $H_2O$/DMSO and assessed for anti-HIV activity in the XTT assay. FIG. 1B is a bar graph of maximum dilution for 50% protection versus HPLC fraction, which illustrates the maximum dilution of each fraction that provided 50% protection from the cytopathic effects of HIV infection for the nonreduced cyanovirin HPLC fractions. Corresponding anti-HIV results for the HPLC fractions from reduced cyanovirin are shown in FIG. 1D, which is a bar graph of maximum dilution for 50% protection versus HPLC fraction. 20% aliquots of selected HPLC fractions were analyzed by SDS-PAGE.

In the initial HPLC separation, using a linear gradient from 30–50% $CH_3CN$, the anti-HIV activity coeluted with the principal UV-absorbing peak at approximately 33% $CH_3CN$. Fractions corresponding to the active peak were pooled and split into two aliquots.

Reinjection of the first aliquot under similar HPLC conditions, but with a linear gradient from 28–38% $CH_3CN$, resolved the active material into two closely eluting peaks at 33.4 and 34.0% $CH_3CN$. The anti-HIV activity profile of the fractions collected during this HPLC run (as shown in FIG. 1B) corresponded with the two UV peaks (as shown in FIG. 1A). SDS-PAGE of fractions collected under the individual peaks showed only a single protein band.

The second aliquot from the original HPLC separation was reduced with β-mercaptoethanol prior to reinjection on the HPLC. Using an identical 28–38% gradient, the reduced material gave one principal peak (as shown in FIG. 1C) that eluted later in the run with 36.8% $CH_3CN$. Only a trace of anti-HIV activity was detected in the HPLC fractions from the reduced material (as shown in FIG. 1D).

The two closely eluting HPLC peaks of the nonreduced material (FIG. 1A) gave only one identical band on SDS-PAGE (run under reducing conditions) and reduction with β-mercaptoethanol resulted in an HPLC peak with a longer retention time than either of the nonreduced peaks. This indicated that disulfides were present in the native protein. Amino acid analysis of the two active peaks showed they had virtually identical compositions. It is possible that the two HPLC peaks resulted from cis/trans isomerism about a proline residue or from microheterogeneity in the protein sample that was not detected in either the amino acid analysis or during sequencing. The material collected as the two HIV-inhibitory peaks was combined for further analyses and was given the name cyanovirin-N.

Example 2

This example illustrates synthesis of cyanovirin genes.

The chemically deduced amino acid sequence of cyanovirin-N was back-translated to obtain a DNA coding sequence. In order to facilitate initial production and purification of recombinant cyanovirin-N, a commercial expression vector (pFLAG-1, from International Biotechnologies, Inc., New Haven, Conn.), for which reagents were available for affinity purification and detection, was selected. Appropriate restriction sites for ligation to pFLAG-1, and a stop codon, were included in the DNA sequence. FIG. 2 is an example of a DNA sequence encoding a synthetic cyanovirin gene. This DNA sequence design couples the cyanovirin-N coding region to codons for a "FLAG" octapeptide at the N-terminal end of cyanovirin, providing for production of a FLAG-cyanovirin fusion protein.

Figure 9:
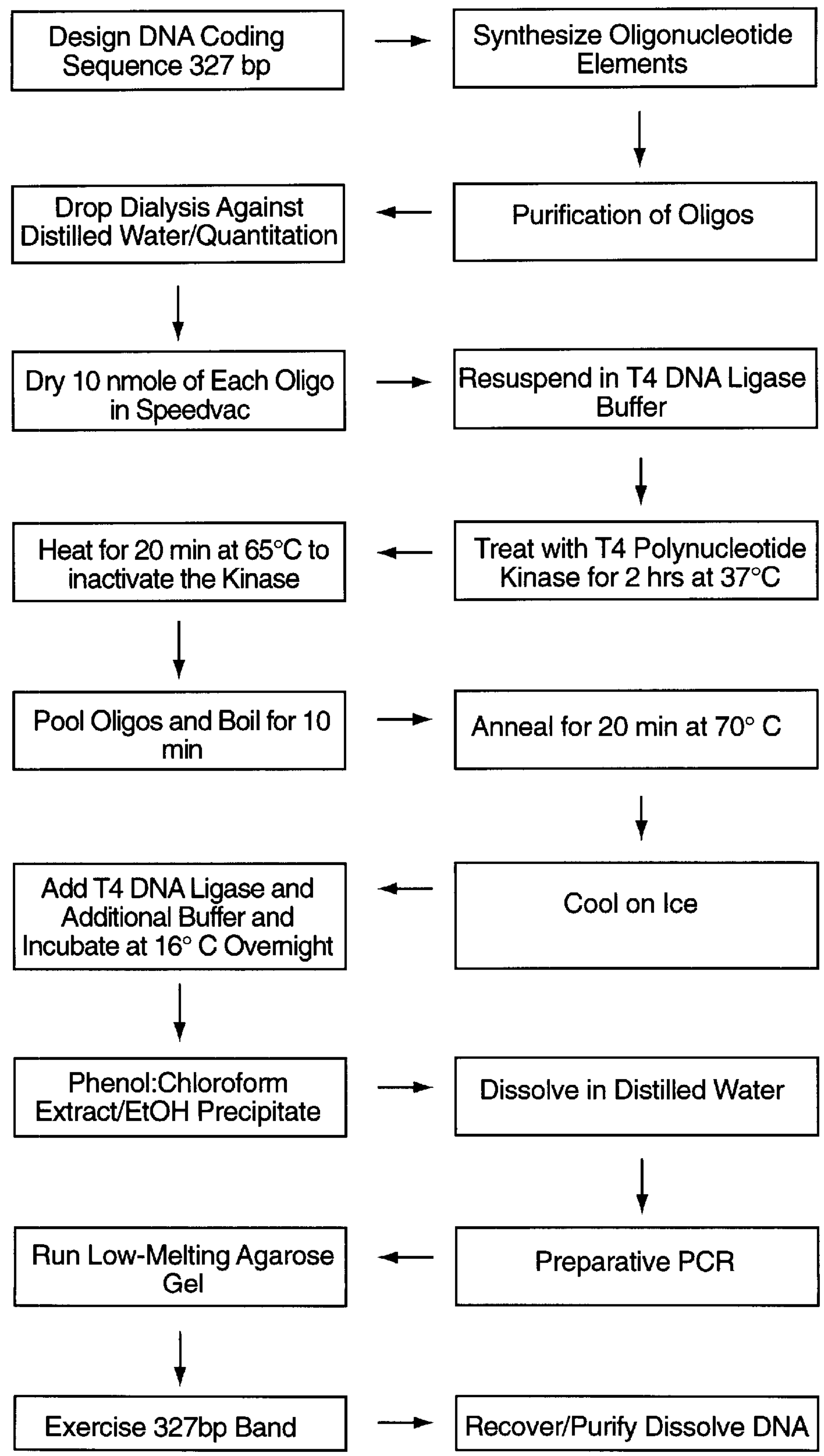
FIG. 9 is a flowchart of the synthesis of the DNA sequence as described in Example 2.

A flowchart for synthesis of this DNA sequence is depicted in FIG. 9. The DNA sequence was synthesized as 13 overlapping, complementary oligonucleotides and assembled to form the double-stranded coding sequence. Oligonucleotide elements of the synthetic DNA coding sequence were synthesized using a dual-column nucleic acid synthesizer (Model 392, Applied-Biosystems Inc., Foster City, Calif.). Completed oligonucleotides were cleaved from the columns and deprotected by incubation overnight at 56° C. in concentrated ammonium hydroxide. Prior to treatment with T4 polynucleotide kinase, 33–66 mers were drop-dialyzed against distilled water. The 13 oligonucleotide preparations were individually purified by HPLC, and 10 nmole quantities of each were ligated with T4 DNA ligase into a 327 bp double-stranded DNA sequence. DNA was recovered and purified from the reaction buffer by phenol:chloroform extraction, ethanol precipitation, and further washing with ethanol. Individual oligonucleotide preparations were pooled and boiled for 10 min to ensure denaturation. The temperature of the mixture was then reduced to 70° C. for annealing of the complementary strands. After 20 min, the tube was cooled on ice and 2,000 units of T4 DNA ligase were added together with additional ligase buffer. Ligation was performed overnight at 16° C. DNA was recovered and purified from the ligation reaction mixture by phenol:chloroform extraction and ethanol precipitation and washing.

The purified, double-stranded synthetic DNA was then used as a template in a polymerase chain reaction (PCR). One μl of the DNA solution obtained after purification of the ligation reaction mixture was used as a template. Thermal cycling was performed using a Perkin-Elmer instrument. "Vent" thermostable DNA polymerase, restriction enzymes, T4 DNA ligase and polynucleotide kinase were obtained from New England Biolabs, Beverly, Mass. Vent polymerase was selected for this application because of its claimed superiority in fidelity compared to the usual Taq enzyme.

The PCR reaction product was run on a 2% agarose gel in TBE buffer. The 327 bp construct was then cut from the gel and purified by electroelution. Because it was found to be relatively resistant to digestion with Hind III and Xho I restriction enzymes, it was initially cloned using the pCR-Script-system (Stratagene). Digestion of a plasmid preparation from one of these clones yielded the coding sequence, which was then ligated into the multicloning site of the pFLAG-1 vector.

*E. coli* were transformed with the pFLAG-construct and recombinant clones were identified by analysis of restriction digests of plasmid DNA. Sequence analysis of one of these selected clones indicated that four bases deviated from the intended coding sequence. This included deletion of three bases coding for one of four cysteine residues contained in the protein and an alteration of the third base in the preceding codon (indicated by the boxes in FIG. 2). In order to correct these "mutations," which presumably arose during the PCR amplification of the synthetic template, a double-stranded "patch" was synthesized, which could be ligated into restriction sites flanking the mutations (these Bst XI and Esp1 sites are also indicated in FIG. 2). The patch was applied and the repair was confirmed by DNA sequence analysis.

Figure 3:
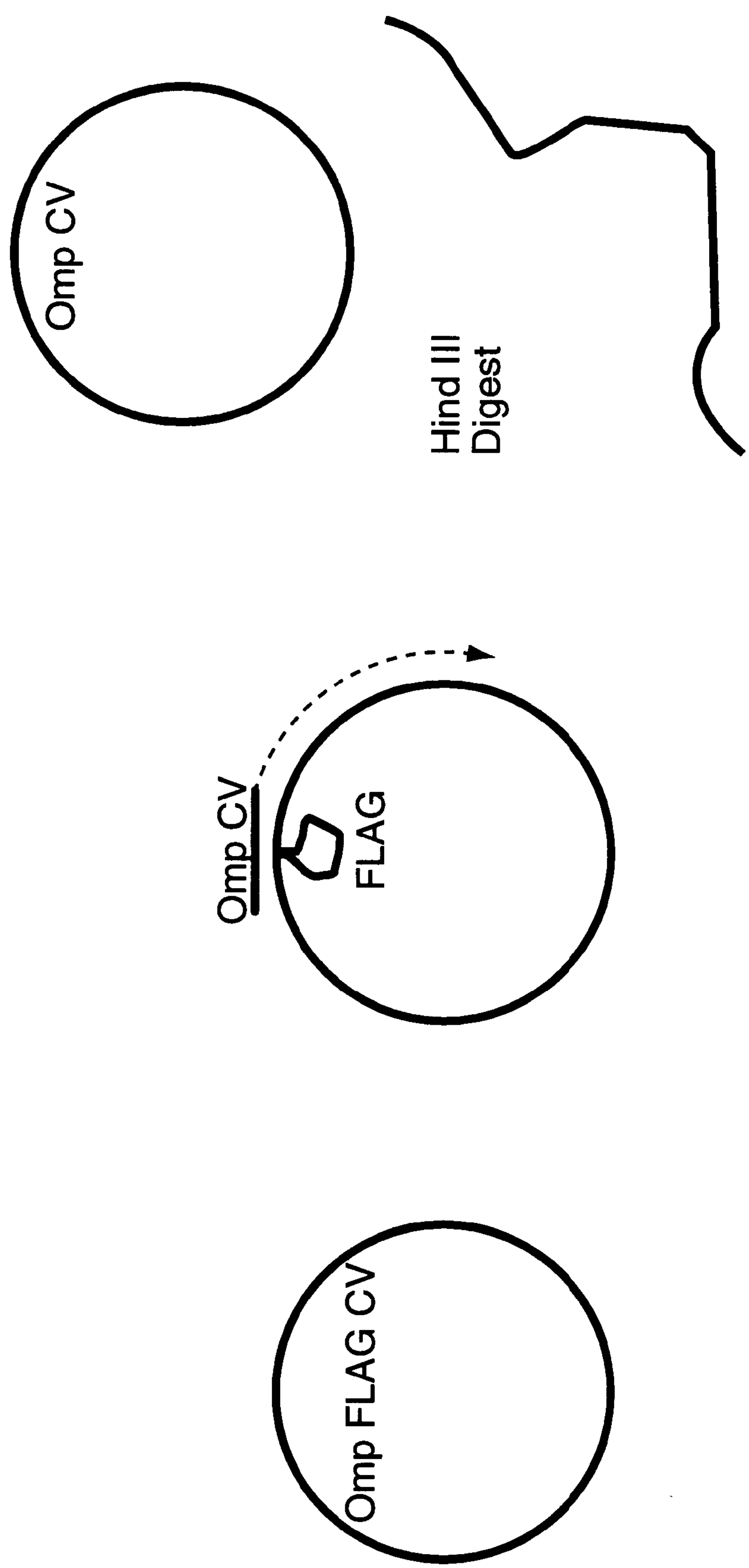
FIG. 3 illustrates a site-directed mutagenesis maneuver used to eliminate codons for a FLAG octapeptide and a Hind III restriction site from the sequence of FIG. 2.

For preparation of a DNA sequence coding for native cyanovirin, the aforementioned FLAG-cyanovirin construct was subjected to site-directed mutagenesis to eliminate the codons for the FLAG octapeptide and, at the same time, to eliminate a unique Hind III restriction site. This procedure is illustrated in FIG. 3, which illustrates a site-directed mutagenesis maneuver used to eliminate codons for a FLAG octapeptide and a Hind III restriction site from the sequence of FIG. 2. A mutagenic oligonucleotide primer was synthesized, which included portions of the codons for the Omp secretory peptide and cyanovirin, but lacking the codons for the FLAG peptide. Annealing of this mutagenic primer, with creation of a DNA hairpin in the template strand, and extension by DNA polymerase resulted in generation of new plasmid DNA lacking both the FLAG codon sequence and the Hind III site (refer to FIG. 2 for details). Digestion of plasmid DNA with Hind III resulted in linearization of "wild-type" strands but not "mutant" strands. Since transformation of *E. coli* occurs more efficiently with circular DNA, clones could be readily selected which had the revised coding sequence which specified production of native cyanovirin-N directly behind the Omp secretory peptide. DNA sequencing verified the presence of the intended sequence. Site-directed mutagenesis reactions were carried out using materials (polymerase, buffers, etc.) obtained from Pharmacia Biotech, Inc., Piscataway, N.J.

Example 3

This example illustrates expression of synthetic cyanovirin genes.

Figure 10:
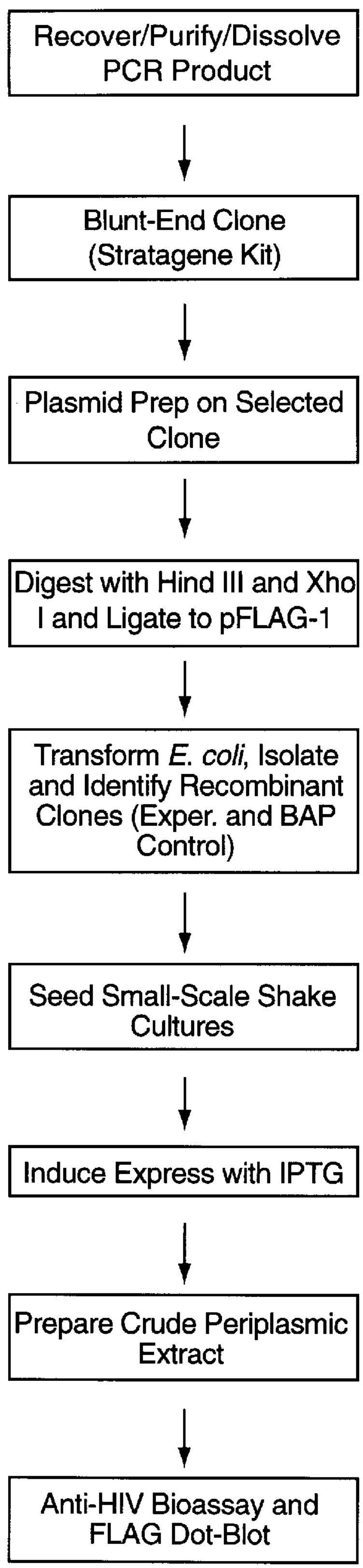
FIG. 10 is a flowchart of the synthesis of the expression of synthetic cyanovirin genes as described in Example 3.

As depicted in FIG. 10, *E. coli* (strain DH5α) were transformed (by electroporation) with the pFLAG-1 vector containing the coding sequence for the FLAG-cyanovirin-N fusion protein (see FIG. 2 for details of the DNA sequence). Selected clones were seeded into small-scale shake flasks containing (LB) growth medium with 100 μg/ml ampicillin and expanded by incubation at 37° C. Larger-scale Erlenmeyer flasks (0.5–3.0 liters) were then seeded and allowed to grow to a density of 0.5–0.7 $OD_{600}$ units. Expression of the FLAG-cyanovirin-N fusion protein was then induced by adding IPTG to a final concentration of 1.7 mM and continuing incubation at 30° C. for 3–6 hrs. For harvesting of periplasmic proteins, bacteria were pelleted, washed, and then osmotically shocked by treatment with sucrose, followed by resuspension in distilled water. Periplasmic proteins were obtained by sedimenting the bacteria and then filtering the aqueous supernatant through Whatman paper. Crude periplasmic extracts showed both anti-HIV activity and presence of a FLAG-cyanovirin-N fusion protein by Western or spot-blotting.

The construct for native cyanovirin-N described in Example 2 was used to transform bacteria in the same manner as described above for the FLAG-cyanovirin-N fusion protein. Cloning, expansion, induction with IPTG, and harvesting were performed similarly. Crude periplasmic extracts showed strong anti-HIV activity on bioassay.

Example 4

This example illustrates purification of recombinant cyanovirin proteins.

Using an affinity column based on an anti-FLAG monoclonal antibody (International Biotechnologies, Inc., New Haven, Conn.), FLAG-cyanovirin-N fusion protein could be purified as depicted in FIG. 11. The respective periplasmic extract, prepared as described in Example 3, was loaded onto 2–20 ml gravity columns containing affinity matrix and washed extensively with PBS containing $CA^{++}$ to remove contaminating proteins. Since the binding of the FLAG peptide to the antibody is $Ca^{++}$-dependent, fusion protein could be eluted by passage of EDTA through the column. Column fractions and wash volumes were monitored by spot-blot analysis using the same anti-FLAG antibody. Fractions containing fusion protein were then pooled, dialyzed extensively against distilled water, and lyophilized.

Figure 4:
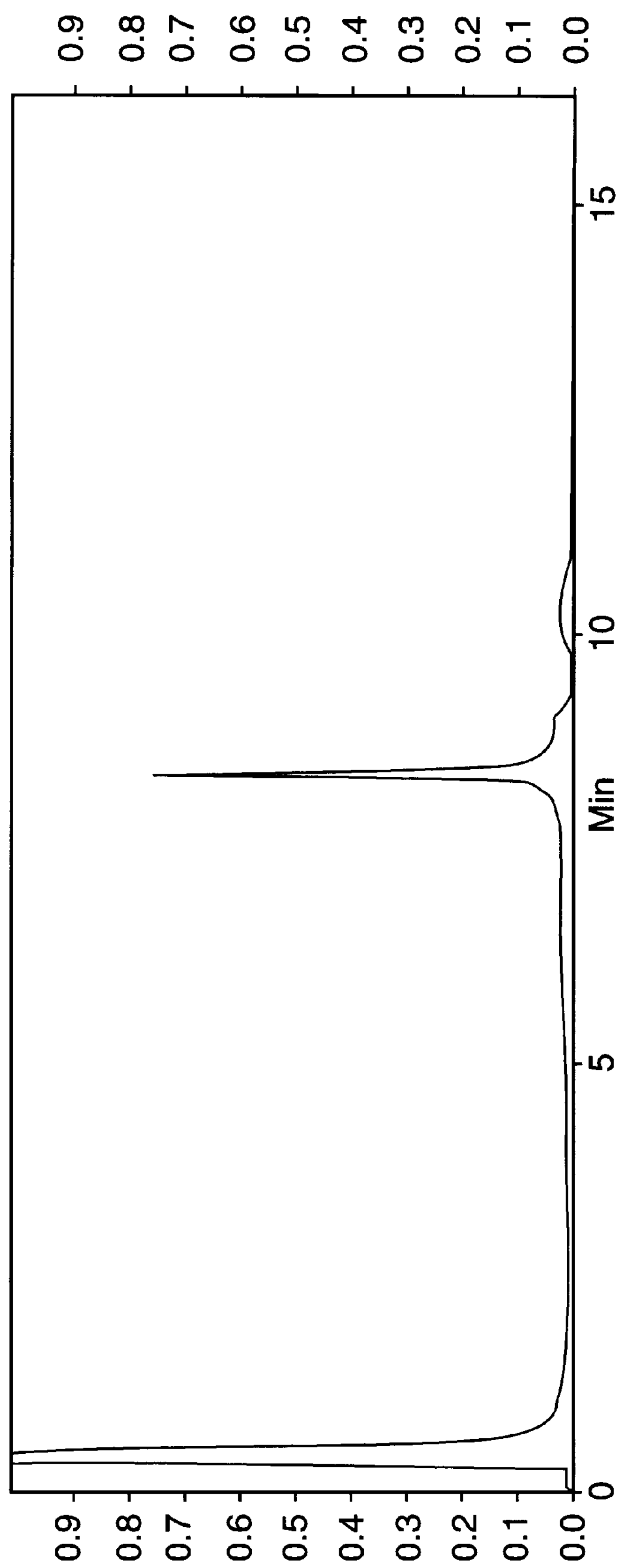
FIG. 4 shows a typical HPLC chromatogram during the purification of a recombinant native cyanovirin.

For purification of recombinant native cyanovirin-N, the corresponding periplasmic extract from Example 3 was subjected to step-gradient $C_4$ reverse-phase, vacuum-liquid chromatography to give three fractions: (1) eluted with 100% $H_2O$, (2) eluted with MeOH—$H_2O$ (2:1), and (3) eluted with 100% MeOH. The anti-HIV activity was concentrated in fraction (2). Purification of the recombinant cyanovirin-N was performed by HPLC on a 1.9×15 cm μBondapak (Waters Associates) $C_{18}$ column eluted with a gradient of increasing concentration of $CH_3CN$ in $H_2O$ (0.05% TFA, v/v in the mobile phase). A chromatogram of the final HPLC purification on a 1×10 cm (Cohensive Technologies, Inc.) $C_4$ column monitored at 280 nm is shown in FIG. 4, which is typical HPLC chromatogram during the purification of a recombinant native cyanovirin. Gradient elution, 5 ml/min, from 100% $H_2O$ to $H_2O$—$CH_3CN$ (7:3) was carried out over 23 min with 0.05% TFA (v/v) in the mobile phase.

Example 5

This example shows anti-HIV activities of natural and recombinant cyanovirin-N and FLAG-cyanovirin-N.

Pure proteins were initially evaluated for antiviral activity using an XTT-tetrazolium anti-HIV assay described previously (Boyd, in *AIDS, Etiology, Diagnosis, Treatment and Prevention,* 1988, supra; Gustafson et al., *J. Med. Chem.* 35, 1978–1986, 1992; Weislow, 1989, supra; and Gulakowski, 1991, supra). The CEM-SS human lymphocytic target cell line used in all assays was maintained in RPMI 1650 medium (Gibco, Grand Island, N.Y.), without phenol red, and was supplemented with 5% fetal bovine serum, 2 mM L-glutamine, and 50 μg/ml gentamicin (complete medium).

Exponentially growing cells were pelleted and resuspended at a concentration of $2.0\times10^5$ cells/ml in complete medium. The Haitian variant of HIV, HTLV-$III_{RF}$ ($3.54\times10^6$ SFU/ml), was used throughout. Frozen virus stock solutions were thawed immediately before use and resuspended in complete medium to yield $1.2\times10^5$ SFU/ml. The appropriate amounts of the pure proteins for anti-HIV evaluations were dissolved in $H_2O$-DMSO (3:1), then diluted in complete medium to the desired initial concentration. All serial drug dilutions, reagent additions, and plate-to-plate transfers were carried out with an automated Biomek 1000 Workstation (Beckman Instruments, Palo Alto, Calif.).

Figure 5A:
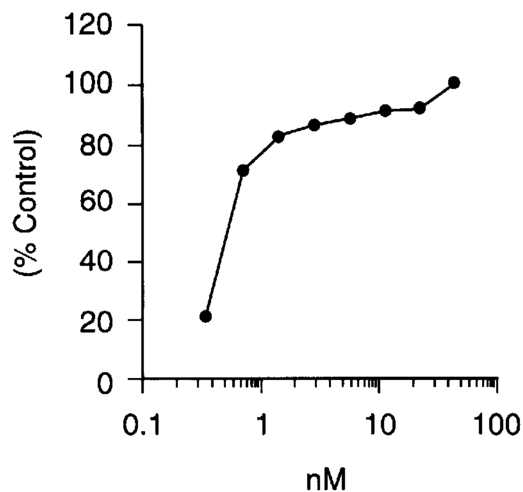
FIG. 5A is a graph of % control versus concentration (nm), which illustrates the antiviral activity of native cyanovirin from *Nostoc ellipsosporum.*
Figure 5B:
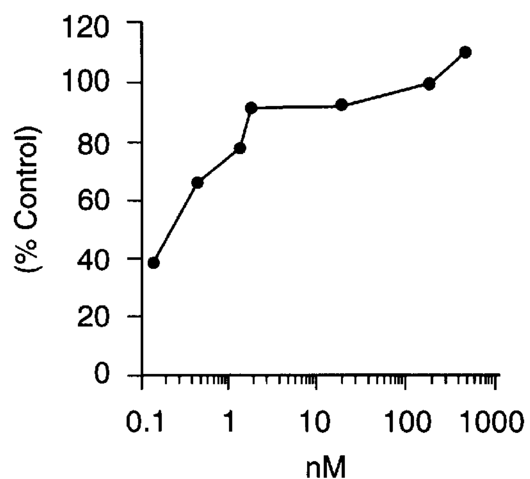
FIG. 5B is a graph of % control versus concentration (nm), which illustrates the antiviral activity of recombinant cyanovirin.
Figure 5C:
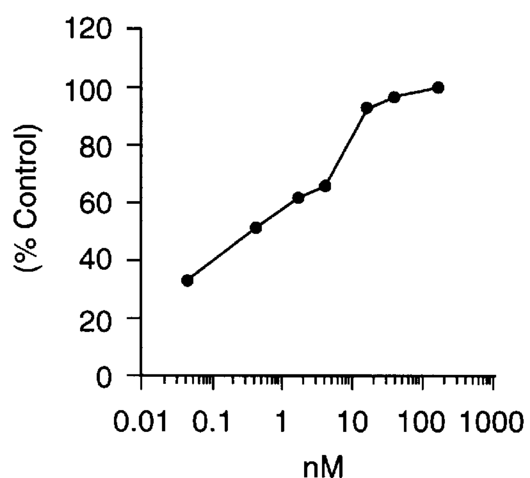
FIG. 5C is a graph of % control versus concentration (nm), which illustrates the antiviral activity of recombinant FLAG-fusion cyanovirin.
Figure 6A:
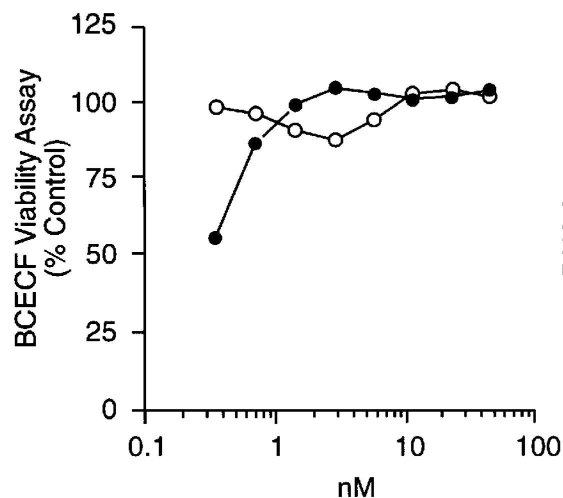
FIG. 6A is a graph of % control versus concentration (nm), which depicts the relative numbers of viable CEM-SS cells infected with HIV-1 in a BCECF assay.
Figure 6B:
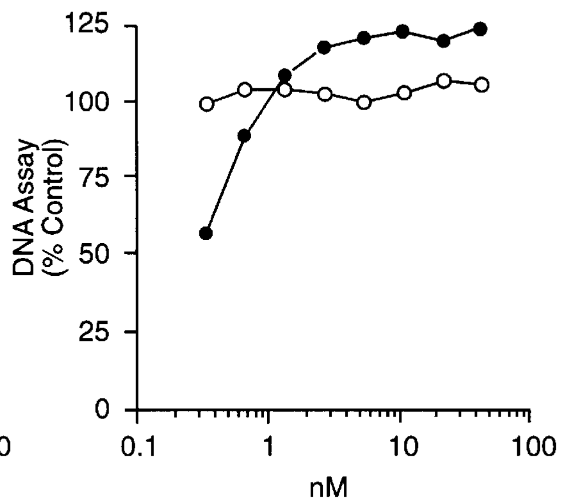
FIG. 6B is a graph of % control versus concentration (nm), which depicts the relative DNA contents of CEM-SS cell cultures infected with HIV-1.
Figure 6C:
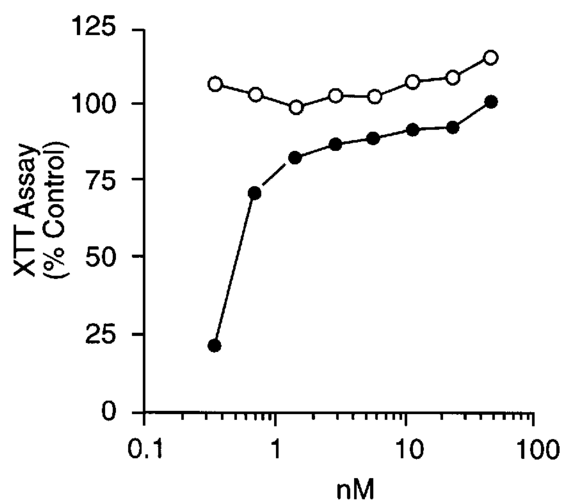
FIG. 6C is a graph of % control versus concentration (nm), which depicts the relative numbers of viable CEM-SS cells infected with HIV-1 in an XTT assay.
Figure 6D:
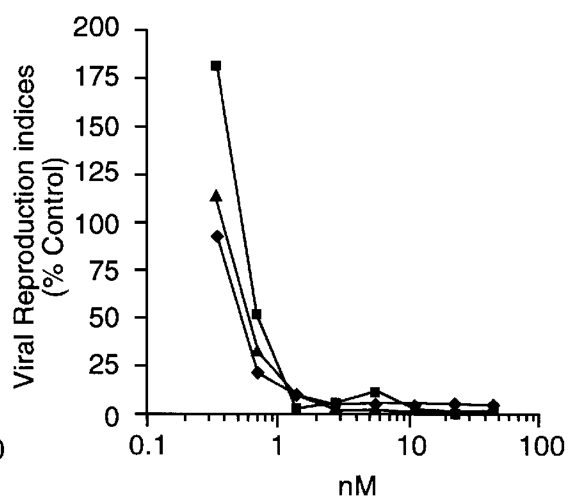
FIG. 6D is a graph of % control versus concentration (nm), which depicts the effect of a range of concentration of cyanovirin upon indices of infectious virus or viral replication.

FIGS. 5A–5C are graphs of % control versus concentration (nm), which illustrate antiviral activities of native cyanovirin from *Nostoc ellipsosporum* (A), recombinant native (B), and recombinant FLAG-fusion (C) cyanovirins. The graphs show the effects of a range of concentrations of the respective cyanovirins upon CEM-SS cells infected with HIV-1 (●), as determined after 6 days in culture. Data points represent the percent of the respective uninfected, nondrug-treated control values. All three cyanovirins showed potent anti-HIV activity, with an $EC_{50}$ in the low nanomolar range and no significant evidence of direct cytotoxicity to the host cells at the highest tested concentrations (up to 1.2 $\mu$M).

As an example of a further demonstration of the anti-HIV activity of pure cyanovirin-N, a battery of interrelated anti-HIV assays was performed in individual wells of 96-well microtiter plates, using methods described in detail elsewhere (Gulakowski, 1991, supra). Briefly, the procedure was as follows. Cyanovirin solutions were serially diluted in complete medium and added to 96-well test plates. Uninfected CEM-SS cells were plated at a density of $1\times10^4$ cells in 50 $\mu$l of complete medium. Diluted HIV-1 was then added to appropriate wells in a volume of 50 $\mu$l to yield a multiplicity of infection of 0.6. Appropriate cell, virus, and drug controls were incorporated in each experiment. The final volume in each microtiter well was 200 $\mu$l. Quadruplicate wells were used for virus-infected cells. Plates were incubated at 37° C. in an atmosphere containing 5% $CO_2$ for 4, 5, or 6 days.

Subsequently, aliquots of cell-free supernatant were removed from each well using the Biomek, and analyzed for reverse transcriptase activity, p24 antigen production, and synthesis of infectious virions as described (Gulakowski, 1991, supra). Cellular growth or viability then was estimated on the remaining contents of each well using the XTT (Weislow et al., 1989, supra), BCECF (Rink et al., *J. Cell Biol.* 95, 189–196, 1982), and DAPI (McCaffrey et al., *In Vitro Cell Develop. Biol.* 24, 247–252, 1988) assays as described (Gulakowski et al., 1991, supra). To facilitate graphical displays and comparisons of data, the individual experimental assay results (of at least quadruplicate determinations of each) were averaged, and the mean values were used to calculate percentages in reference to the appropriate controls. Standard errors of the mean values used in these calculations typically averaged less than 10% of the respective mean values.

FIGS. 6A–6D are graphs of % control versus concentration (nm), which illustrate anti-HIV activity of a cyanovirin in a multiparameter assay format. Graphs 6A, 6B, and 6C show the effects of a range of concentrations of cyanovirin upon uninfected CEM-SS cells (○), and upon CEM-SS cells infected with HIV-1 (●), as determined after 6 days in culture. Graph 6A depicts the relative numbers of viable CEM-SS cells, as assessed by the BCECF assay. Graph 6B depicts the relative DNA contents of the respective cultures. Graph 6C depicts the relative numbers of viable CEM-SS cells, as assessed by the XTT assay. Graph 6D shows the effects of a range of concentrations of cyanovirin upon indices of infectious virus or viral replication as determined after 4 days in culture. These indices include viral reverse transcriptase (▲), viral core protein p24 (♦), and syncytium-forming units (■). In graphs 6A, 6B, and 6C, the data are represented as the percent of the uninfected, nondrug-treated control values. In graph 6D the data are represented as the percent of the infected, nondrug-treated control values.

As illustrated in FIG. 6, cyanovirin-N was capable of complete inhibition of the cytopathic effects of HIV-1 upon CEM-SS human lymphoblastoid target cells in vitro; direct cytotoxicity of the protein upon the target cells was not observed at the highest tested concentrations. Cyanovirin-N also strikingly inhibited the production of RT, p24, and SFU in HIV-1-infected CEM-SS cells within these same inhibitory effective concentrations, indicating that the protein halted viral replication.

The anti-HIV activity of the cyanovirins is extremely-resilient to harsh environmental challenges. For example, unbuffered cyanovirin-N solutions withstood repeated freeze-thaw cycles or dissolution in organic solvents (up to 100% DMSO, MeOH, or $CH_3CN$) with no loss of activity. Cyanovirin-N tolerated detergent (0.1% SDS), high salt (6 M guanidine HCl) and heat treatment (boiling, 10 min in $H_2O$) with no significant loss of HIV-inhibitory activity. Reduction of the disulfides with β-mercaptoethanol, followed immediately by $C_{18}$ HPLC purification, drastically reduced the cytoprotective activity of cyanovirin-N. However, solutions of reduced cyanovirin-N regained anti-HIV inhibitory activity during prolonged storage. When cyanovirin-N was reduced (β-mercaptoethanol, 6M guanidine HCl, pH 8.0) but not put through $C_{18}$ HPLC, and, instead, simply desalted, reconstituted and assayed, it retained virtually full activity.

Example 6

This example illustrates that the HIV viral envelope gp120 is a principal molecular target of cyanovirin-N.

Figures 7A, 7B:
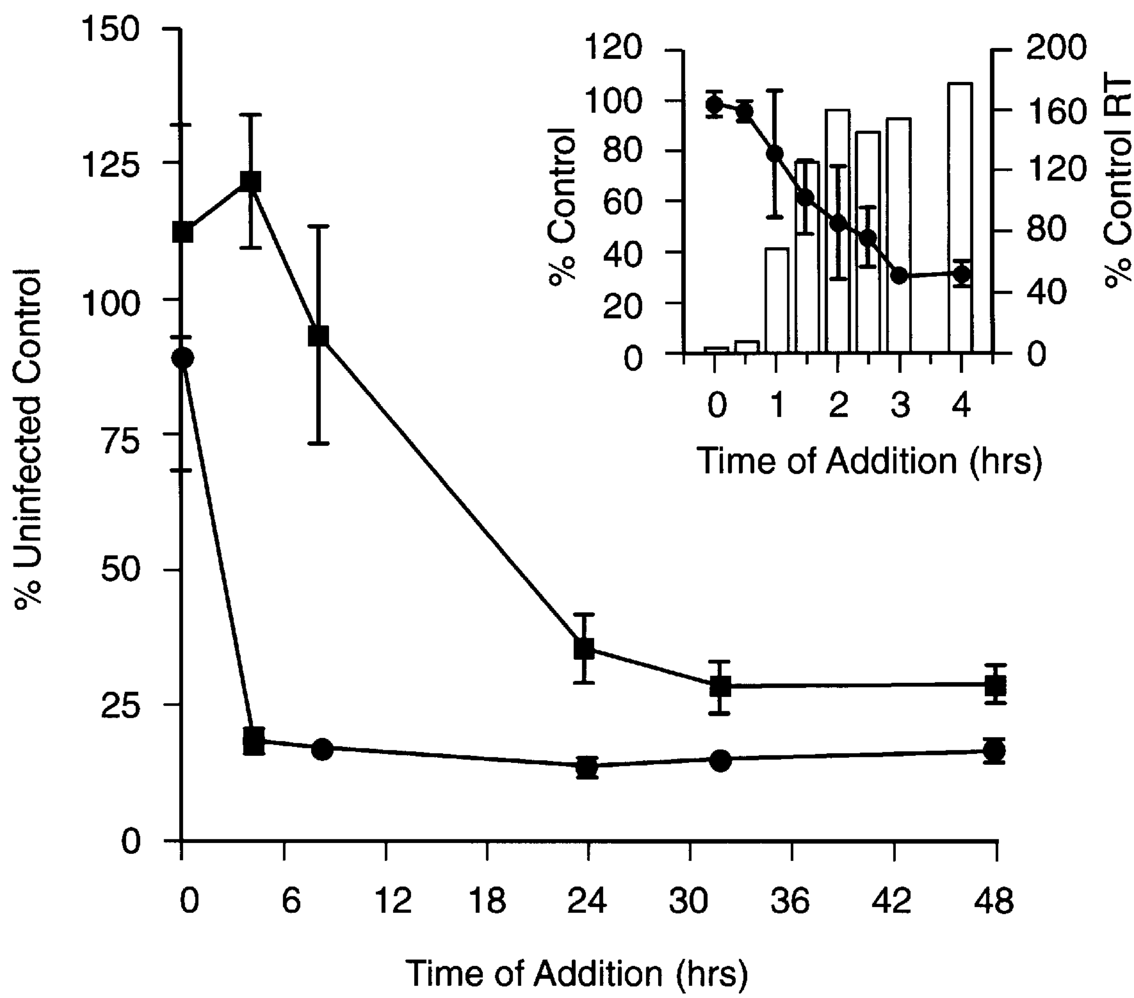
FIG. 7A is a graph of % uninfected control versus time of addition (hrs), which shows results of time-of-addition studies of a cyanovirin, showing anti-HIV activity in CEM-SS cells infected with HIV-$1_{RF}$.
FIG. 7B is a bar graph of % control versus time of addition (hrs) versus % control RT (reverse transcriptase).

Initial experiments, employing the XTT-tetrazolium assay (Weislow et al., 1989, supra), revealed that host cells pre-incubated with cyanovirin (10 nM, 1 hr), then centrifuged free of cyanovirin-N, retained normal susceptibility to HIV infection; in contrast, the infectivity of concentrated virus similarly pretreated, then diluted to yield non-inhibitory concentrations of cyanovirin-N, was essentially abolished. This indicated that cyanovirin-N was acting directly upon the virus itself, i.e., acting as a direct "virucidal" agent to prevent viral infectivity even before it could enter the host cells. This was further confirmed in time-of-addition experiments, likewise employing the XTT-tetrazolium assay (Weislow, 1989, supra), which showed that, to afford maximum antiviral activity, cyanovirin-N had to be added to cells before or as soon as possible after addition of virus as shown in FIG. 7, which is a graph of % uninfected control versus time of addition (hrs), which shows results of time-of-addition studies of a cyanovirin, showing anti-HIV activity in CEM-SS cells infected with HIV-$1_{RF}$. Introduction of cyanovirin (●) or ddC (■) (10 nM and 5 $\mu$M concentrations, respectively) was delayed by various times after initial incubation, followed by 6 days incubation, then assay of cellular viability (FIG. 7A) and RT (open bars, inset). Points represent averages (±S.D.) of at least triplicate determinations. In marked contrast to the reverse transcriptase inhibitor ddC, delay of addition of cyanovirin-N by only 3 hrs resulted in little or no antiviral activity (FIG. 7B). The aforementioned results suggested that cyanovirin-N inhibited HIV-infectivity by interruption of the initial interaction of the virus with the cell; this would, therefore, likely involve a direct interaction of cyanovirin-N with the viral gp120. This was confirmed by ultrafiltration experiments and dot-blot assays.

Ultrafiltration experiments were performed to determine if soluble gp120 and cyanovirin-N could bind directly, as assessed by inhibition of passage of cyanovirin-N through a 50 kDa-cutoff ultrafilter. Solutions of cyanovirin (30 μg) in PBS were treated with various concentrations of gp120 for 1 hr at 37° C., then filtered through a 50 kDa-cutoff centrifugal ultrafilter (Amicon). After washing 3 times with PBS, filtrates were desalted with 3 kDa ultrafilters; retentates were lyophilized, reconstituted in 100 μl $H_2O$ and assayed for anti-HIV activity.

Figure 8:
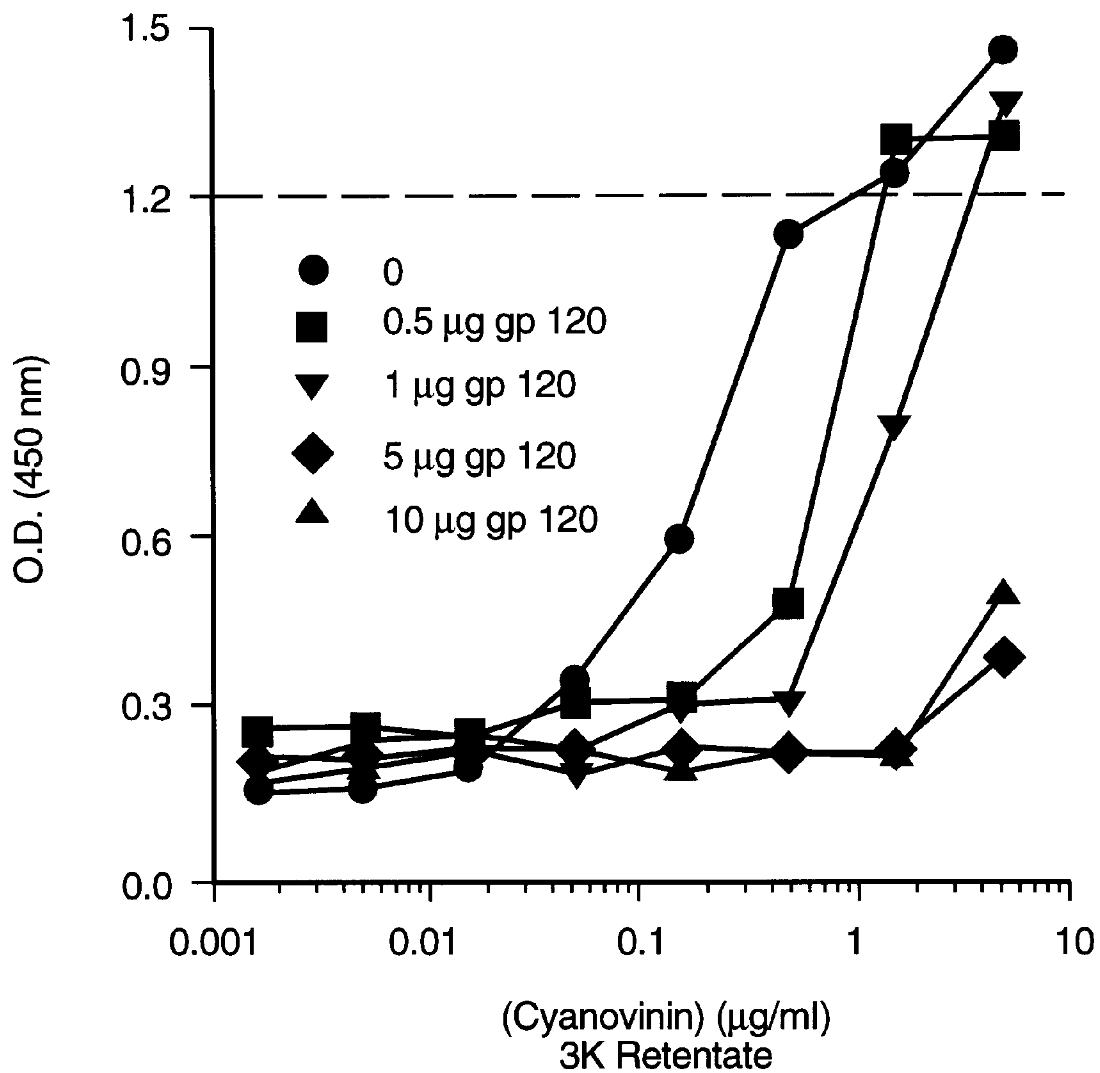
FIG. 8 is a graph of OD (450 nm) versus cyanovirin concentration ($\mu$g/ml), which illustrates cyanovirin/gp120 interactions defining gp120 as a principal molecular target of cyanovirin.

FIG. 8 is a graph of OD (450 nm) versus cyanovirin concentration (μg/ml), which illustrates cyanovirin/gp120 interactions defining gp120 as a principal molecular target of cyanovirin. Free cyanovirin-N was readily eluted, as evidenced by complete recovery of cyanovirin-N bioactivity in the filtrate. In contrast, filtrates from cyanovirin-N solutions treated with gp120 revealed a concentration-dependent loss of filtrate bioactivity; moreover, the 50 kDa filter retentates were all inactive, indicating that cyanovirin-N and soluble gp120 interacted directly to form a complex incapable of binding to gp120 of intact virus.

There was further evidence of a direct interaction of cyanovirin-N and gp120 in a PVDF membrane dot-blot assay. A PVDF membrane was spotted with 5 μg CD4 (CD), 10 μg aprotinin (AP), 10 μg bovine globulin (BG), and decreasing amounts of cyanovirin; 6 μg [1], 3 μg [2], 1.5 μg [3], 0.75 μg [4], 0.38 μg [5], 0.19 μg [6], 0.09 μg [7], and 0.05 μg [8], then washed with PBST and visualized per manufacturer's recommendations. A dot blot of binding of cyanovirin and a gp120-HRP conjugate (Invitrogen) showed that cyanovirin-N specifically bound a horseradish peroxidase conjugate of gp120 (gp120-HRP) in a concentration-dependent manner.

All of the references cited herein are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method of obtaining an antiviral protein or antiviral peptide from *Nostoc ellipsosporum*, which method comprises:

(a) identifying an extract of *Nostoc ellipsosporum* containing antiviral activity, (b) optionally removing high molecular weight biopolymers from said extract, (c) antiviral bioassay-guided fractionating said extract to obtain a crude extract of said protein or peptide, and (d) purifying said crude extract by reverse-phase HPLC to obtain said protein or peptide.

2. The method of claim 1, wherein said antiviral protein or antiviral peptide comprises at least nine contiguous amino acids of SEQ ID NO:2.

3. The method of claim 1, wherein said antiviral protein or antiviral peptide comprises the amino acid sequence of SEQ ID NO:2 or a fragment thereof, wherein said fragment has antiviral activity.

* * * * *

```
                        SEQUENCE LISTING

(1) GENERAL INFORMATION:

   (iii) NUMBER OF SEQUENCES: 4


(2) INFORMATION FOR SEQ ID NO:1:

     (i) SEQUENCE CHARACTERISTICS:
          (A) LENGTH: 327 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 10..312

    (xi) SEQUENCE DESCRIPTION: SEQ ID NO:1:

CGATCGAAG CTT GGT AAA TTC TCC CAG ACC TGC TAC AAC TCC GCT ATC         48
          Leu Gly Lys Phe Ser Gln Thr Cys Tyr Asn Ser Ala Ile
            1               5                  10

CAG GGT TCC GTT CTG ACC TCC ACC TGC GAA CGT ACC AAC GGT GGT TAC       96
Gln Gly Ser Val Leu Thr Ser Thr Cys Glu Arg Thr Asn Gly Gly Tyr
     15                  20                  25

AAC ACC TCC TCC ATC GAC CTG AAC TCC GTT ATC GAA AAC GTT GAC GGT      144
Asn Thr Ser Ser Ile Asp Leu Asn Ser Val Ile Glu Asn Val Asp Gly
 30                  35                  40                  45

TCC CTG AAA TGG CAG CCG TCC AAC TTC ATC GAA ACC TGC CGT AAC ACC      192
Ser Leu Lys Trp Gln Pro Ser Asn Phe Ile Glu Thr Cys Arg Asn Thr
                 50                  55                  60

CAG CTG GCT GGT TCC TCC GAA CTG GCT GCT GAA TGC AAA ACC CGT GCT      240
Gln Leu Ala Gly Ser Ser Glu Leu Ala Ala Glu Cys Lys Thr Arg Ala
             65                  70                  75

CAG CAG TTC GTT TCC ACC AAA ATC AAC CTG GAC GAC CAC ATC GCT AAC      288
Gln Gln Phe Val Ser Thr Lys Ile Asn Leu Asp Asp His Ile Ala Asn
         80                  85                  90

ATC GAC GGT ACC CTG AAA TAC GAA TAACTCGAGA TCGTA                     327
Ile Asp Gly Thr Leu Lys Tyr Glu
```

```
     95                  100


(2) INFORMATION FOR SEQ ID NO:2:

     (i) SEQUENCE CHARACTERISTICS:
          (A) LENGTH: 101 amino acids
          (B) TYPE: amino acid
          (D) TOPOLOGY: linear

    (ii) MOLECULE TYPE: protein

    (xi) SEQUENCE DESCRIPTION: SEQ ID NO:2:

Leu Gly Lys Phe Ser Gln Thr Cys Tyr Asn Ser Ala Ile Gln Gly Ser
  1               5                  10                  15

Val Leu Thr Ser Thr Cys Glu Arg Thr Asn Gly Gly Tyr Asn Thr Ser
             20                  25                  30

Ser Ile Asp Leu Asn Ser Val Ile Glu Asn Val Asp Gly Ser Leu Lys
         35                  40                  45

Trp Gln Pro Ser Asn Phe Ile Glu Thr Cys Arg Asn Thr Gln Leu Ala
     50                  55                  60

Gly Ser Ser Glu Leu Ala Ala Glu Cys Lys Thr Arg Ala Gln Gln Phe
 65                  70                  75                  80

Val Ser Thr Lys Ile Asn Leu Asp Asp His Ile Ala Asn Ile Asp Gly
                 85                  90                  95

Thr Leu Lys Tyr Glu
            100


(2) INFORMATION FOR SEQ ID NO:3:

     (i) SEQUENCE CHARACTERISTICS:
          (A) LENGTH: 327 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 1..327

    (xi) SEQUENCE DESCRIPTION: SEQ ID NO:3:

GAC TAC AAG GAC GAC GAT GAC AAG CTT GGT AAA TTC TCC CAG ACC TGC        48
Asp Tyr Lys Asp Asp Asp Asp Lys Leu Gly Lys Phe Ser Gln Thr Cys
  1               5                  10                  15

TAC AAC TCC GCT ATC CAG GGT TCC GTT CTG ACC TCC ACC TGC GAA CGT        96
Tyr Asn Ser Ala Ile Gln Gly Ser Val Leu Thr Ser Thr Cys Glu Arg
             20                  25                  30

ACC AAC GGT GGT TAC AAC ACC TCC TCC ATC GAC CTG AAC TCC GTT ATC       144
Thr Asn Gly Gly Tyr Asn Thr Ser Ser Ile Asp Leu Asn Ser Val Ile
         35                  40                  45

GAA AAC GTT GAC GGT TCC CTG AAA TGG CAG CCG TCC AAC TTC ATC GAA       192
Glu Asn Val Asp Gly Ser Leu Lys Trp Gln Pro Ser Asn Phe Ile Glu
     50                  55                  60

ACC TGC CGT AAC ACC CAG CTG GCT GGT TCC TCC GAA CTG GCT GCT GAA       240
Thr Cys Arg Asn Thr Gln Leu Ala Gly Ser Ser Glu Leu Ala Ala Glu
 65                  70                  75                  80

TGC AAA ACC CGT GCT CAG CAG TTC GTT TCC ACC AAA ATC AAC CTG GAC       288
Cys Lys Thr Arg Ala Gln Gln Phe Val Ser Thr Lys Ile Asn Leu Asp
                 85                  90                  95

GAC CAC ATC GCT AAC ATC GAC GGT ACC CTG AAA TAC GAA                   327
Asp His Ile Ala Asn Ile Asp Gly Thr Leu Lys Tyr Glu
            100                 105
```

-continued

```
(2) INFORMATION FOR SEQ ID NO:4:

     (i) SEQUENCE CHARACTERISTICS:
          (A) LENGTH: 109 amino acids
          (B) TYPE: amino acid
          (D) TOPOLOGY: linear

    (ii) MOLECULE TYPE: protein

    (xi) SEQUENCE DESCRIPTION: SEQ ID NO:4:

Asp Tyr Lys Asp Asp Asp Asp Lys Leu Gly Lys Phe Ser Gln Thr Cys
  1               5                  10                  15

Tyr Asn Ser Ala Ile Gln Gly Ser Val Leu Thr Ser Thr Cys Glu Arg
             20                  25                  30

Thr Asn Gly Gly Tyr Asn Thr Ser Ser Ile Asp Leu Asn Ser Val Ile
         35                  40                  45

Glu Asn Val Asp Gly Ser Leu Lys Trp Gln Pro Ser Asn Phe Ile Glu
     50                  55                  60

Thr Cys Arg Asn Thr Gln Leu Ala Gly Ser Ser Glu Leu Ala Ala Glu
 65                  70                  75                  80

Cys Lys Thr Arg Ala Gln Gln Phe Val Ser Thr Lys Ile Asn Leu Asp
                 85                  90                  95

Asp His Ile Ala Asn Ile Asp Gly Thr Leu Lys Tyr Glu
            100                 105
```